(12) United States Patent
Tatsui et al.

(10) Patent No.: US 11,065,063 B2
(45) Date of Patent: Jul. 20, 2021

(54) UTILIZATION OF LASER INTERSTITIAL THERMOTHERAPY GUIDED WITH REAL TIME THERMAL MRI

(71) Applicant: Board of Regents, The University of Texas System, Austin, TX (US)

(72) Inventors: Claudio E. Tatsui, Pearland, TX (US); R. Jason Stafford, Houston, TX (US)

(73) Assignee: Board of Regents, The University of Texas System, Austin, TX (US)

(*) Notice: Subject to any disclaimer, the term of this patent is extended or adjusted under 35 U.S.C. 154(b) by 640 days.

(21) Appl. No.: 15/741,423

(22) PCT Filed: Jul. 1, 2016

(86) PCT No.: PCT/US2016/040632
§ 371 (c)(1),
(2) Date: Jan. 2, 2018

(87) PCT Pub. No.: WO2017/004482
PCT Pub. Date: Jan. 5, 2017

(65) Prior Publication Data
US 2018/0368918 A1    Dec. 27, 2018

Related U.S. Application Data

(60) Provisional application No. 62/188,250, filed on Jul. 2, 2015.

(51) Int. Cl.
*A61B 34/20* (2016.01)
*A61B 5/055* (2006.01)
(Continued)

(52) U.S. Cl.
CPC .............. *A61B 34/20* (2016.02); *A61B 5/01* (2013.01); *A61B 5/055* (2013.01); *A61B 5/064* (2013.01);
(Continued)

(58) Field of Classification Search
CPC ...... A61N 2005/067; A61N 2005/0612; A61N 2005/0659; A61B 18/24; A61B 2018/0044; A61B 2018/00577; A61B 2018/00642; A61B 2018/00678; A61B 2018/00708; A61B 2018/00791; A61B 2018/00809;
(Continued)

(56) References Cited

U.S. PATENT DOCUMENTS

| | | | |
|---|---|---|---|
| 5,855,554 A | 1/1999 | Schneider et al. | |
| 6,122,541 A * | 9/2000 | Cosman ............... | A61B 90/10 600/426 |

(Continued)

OTHER PUBLICATIONS

Attaar et al., "Accuracy of Laser Placement With Frameless Stereotaxy in Magnetic Resonance-Guided Laser-Induced Thermal Therapy," *Oper. Neurosurg.*, 11(4):554-563, 2015.
(Continued)

*Primary Examiner* — Amelie R Davis
(74) *Attorney, Agent, or Firm* — Parker Highlander PLLC

(57) ABSTRACT

Methods, apparatus, and kits for applying thermal energy to tissue in a region of interest. Certain embodiments include registration of fiducial markers with an image guidance system and temperature monitoring via magnetic resonance imaging thermography.

14 Claims, 13 Drawing Sheets

(51) Int. Cl.

| | |
|---|---|
| *A61B 5/01* | (2006.01) |
| *A61B 5/06* | (2006.01) |
| *A61B 90/10* | (2016.01) |
| *A61B 90/11* | (2016.01) |
| *A61B 18/24* | (2006.01) |
| *A61B 18/22* | (2006.01) |
| *A61B 18/20* | (2006.01) |
| *A61B 18/00* | (2006.01) |
| *A61N 5/067* | (2006.01) |
| *A61N 5/06* | (2006.01) |
| *A61B 90/00* | (2016.01) |

(52) U.S. Cl.
CPC .............. *A61B 18/24* (2013.01); *A61B 90/10* (2016.02); *A61B 90/11* (2016.02); *A61B 2018/0044* (2013.01); *A61B 2018/00577* (2013.01); *A61B 2018/00642* (2013.01); *A61B 2018/00678* (2013.01); *A61B 2018/00708* (2013.01); *A61B 2018/00791* (2013.01); *A61B 2018/00809* (2013.01); *A61B 2018/20361* (2017.05); *A61B 2018/2205* (2013.01); *A61B 2034/207* (2016.02); *A61B 2034/2051* (2016.02); *A61B 2034/2055* (2016.02); *A61B 2090/363* (2016.02); *A61B 2090/374* (2016.02); *A61B 2090/3954* (2016.02); *A61B 2090/3983* (2016.02); *A61N 2005/067* (2013.01); *A61N 2005/0612* (2013.01); *A61N 2005/0659* (2013.01)

(58) Field of Classification Search
CPC .. A61B 2018/20361; A61B 2018/2205; A61B 2034/2051; A61B 2034/2055; A61B 2034/207; A61B 2034/2072; A61B 2090/363; A61B 2090/374; A61B 2090/3954; A61B 2090/3983; A61B 34/20; A61B 5/01; A61B 5/055; A61B 5/064; A61B 90/10; A61B 90/11
See application file for complete search history.

(56) References Cited

U.S. PATENT DOCUMENTS

| | | | |
|---|---|---|---|
| 6,419,680 | B1 | 7/2002 | Cosman et al. |
| 2003/0023236 | A1 | 1/2003 | Gowda et al. |
| 2003/0187351 | A1 | 10/2003 | Franck et al. |
| 2004/0059328 | A1 | 3/2004 | Daniel et al. |
| 2005/0054900 | A1 | 3/2005 | Mawn et al. |
| 2005/0113668 | A1 | 5/2005 | Srinivasan |
| 2006/0147100 | A1 | 7/2006 | Fitzpatrick |
| 2008/0275331 | A1* | 11/2008 | Tseng ................. G01R 33/4804 600/411 |
| 2010/0010505 | A1 | 1/2010 | Herlihy et al. |
| 2011/0295143 | A1* | 12/2011 | Leuthardt ............ A61B 5/0476 600/544 |
| 2013/0217996 | A1 | 8/2013 | Finkelstein et al. |
| 2015/0078535 | A1* | 3/2015 | DeSena .................. A61B 90/39 378/204 |
| 2015/0089763 | A1 | 3/2015 | Lv |

OTHER PUBLICATIONS

Carpentier et al., "MR-guided laser-induced thermal therapy (LITT) for recurrent glioblastomas," *Lasers Surgery Med.*, 44(5):361-368, 2012.

Carpentier et al., "Real-Time Magnetic Resonance-Guided Laser Thermal Therapy for Focal Metatstatic Brain Tumors," *Neurosurgery*, 63(supplement 1):ONS21-ONS29, 2008.

International Preliminary Report on Patentability issued in corresponding PCT Application No. PCT/US16/040632, dated Jan. 11, 2018.

International Search Report and Written Opinion issued in corresponding PCT Application No. PCT/US16/040632, dated Sep. 15, 2016.

Medtronic, Inc., "Visualase® MRI-guided Laser Ablation for Minimally Invasive Neurosurgery," <URL: https://www.youtube.com/watch?v=okpWbBVhZVE>, 2014.

Patel et al., "Frameless Stereotactic Magnetic Resonance Imaging-Guided Laser Interstitial Thermal Therapy to Perform Bilateral Anterior Cingulotomy for Intractable Pain: Feasibility Technical Aspects, and Initial Experience in 3 Patients," *Neurosurgery*, 11(1):17-25, 2015.

\* cited by examiner

UTILIZATION OF LASER INTERSTITIAL THERMOTHERAPY GUIDED WITH REAL TIME THERMAL MRI

CROSS-REFERENCE TO RELATED APPLICATIONS

This application is a national phase application under 35 U.S.C. § 371 of International Application No. PCT/US2016/040632, filed Jul. 1, 2016, which claims priority to U.S. Provisional Patent Application Ser. No. 62/188,250 filed Jul. 2, 2015, the contents of each of which are incorporated herein by reference.

BACKGROUND INFORMATION

The ability to precisely locate medical instruments during surgical procedures is particularly important when direct visualization is not feasible, including for example stereotactic brain and spine surgery or percutaneous biopsies. Existing systems encounter difficulties in locating and tracking the movement of instruments during such procedures. For example, many medical instruments are not compatible with magnetic resonance imaging (MRI), and therefore are not suited for such visualization techniques.

In addition, the use of fiducial markers to register the position of instruments can create challenges in certain regions, including for example near the spine. Fiducial markers can easily move on the loose skin of the dorsal region. For example, placement of the reference array of markers on the spinous process after the MRI is completed moves the skin (and fiducial markers) creating unacceptable error. Other imaging techniques, such as computed tomography (CT) also present challenges. For example, while CT fluoromatch may present acceptable results for the lumbar region, its use becomes difficult for lower thoracic (T7-12), more difficult for mid thoracic (T3-6) and is not feasible for T1-2 (shoulders).

The utilization of intraoperative cone beam CT scan, 3D fluoroscopy or intraoperative CT scans can overcome some of the inaccuracies since the reference image is obtained with the patient in the final operative position, however, visualization of soft tissue (blood vessels, internal organs, spinal cord) is a limitation of the method.

Without the ability to obtain images to confirm accuracy of computer based navigation during the surgical procedure, errors can occur due to mismatch between the real position of an instrument and the interactive reconstructed images demonstrated on the screen of the image guidance system. Such positioning errors can create unwanted effects, including damaging healthy tissue proximal to the target tissue.

The management of metastatic disease to certain areas, including those around the spine, is multimodal and involves a multidisciplinary approach with roles played by oncologists who deliver chemo/hormonal/immunotherapy in an attempt to achieve systemic control, radiation oncologists who deliver radiation to the tumor, aiming at local control and surgeons, who provide spinal stabilization and immediate neural element decompression, aiming at preservation of neurological function, spinal stability, and symptom relief [6, 19]. Unfortunately, these aims must be balanced against each other, with local control and functional preservation generally taking priority over systemic control in most acute presentations.

In cases with high degree of spinal cord compression, the most common surgical approach for the thoracic and lumbar spine involves a laminectomy with pedicle screw stabilization [2, 28, 29] and for the cervical spine, an anterior approach with vertebral column reconstruction [30, 31]. In either case, surgical intervention delays systemic treatment (usually for 3-4 weeks) while patients recover functional status, wounds heal, and post-operative radiation is delivered.

Knowledge of tumor histology is fundamental in the management of spinal metastasis, even in cases of a suspected primary tumor, histological confirmation is needed for treatment planning. In general, radiation is well tolerated by patients and the conventional regimen of 30 Gy in 10 fractions is commonly used even in cases of terminal disease [5, 32, 33]. The notion that conventional radiotherapy confers a palliative benefit comes from studies that compared this modality with lumbar and thoracic laminectomy, which used maintenance and recovery of ambulation as an outcome measure [1-4, 8, 34]. It is known that some histologies are more sensitive to conventional radiation (breast, prostate, hematological) than others (lung, renal cell carcinoma) [1, 6, 8, 33]. Recent advancements in technology, however, have allowed for the delivery of high doses of highly conformed radiation capable of overcoming this radioresistance to conventional radiotherapy. Recent series have demonstrated improvement in local control, pain, and quality of life of patients treated with this modality [10-16, 35].

Bilsky et al. [3] have proposed a decision framework based on neurological, oncological, mechanical and systemic considerations (NOMS) [6] in which the judicious use of surgery and conventional and stereotactic radiation are combined to provide optimal local control, symptomatic relief, and functional preservation for patients suffering from spinal metastasis [3, 6, 18-20]. These authors advocate surgery only in cases of high degree of spinal cord compression, in recognition of the fact that tumoricidal doses of radiation can be delivered with the stereotactic method up to but not inclusive of a margin of 2-3 mm around the spinal cord [3, 18]. In cases where radio-resistant histologies with epidural extension have violated this 2-3 mm margin, they advocate a surgical approach in which the goal is spinal stabilization and resection of the epidural tumor, not intending to achieve a gross total resection (separation surgery). This approach avoids complex reconstruction of the vertebral bodies, decreases the surgical time and blood loss, thus facilitating a more rapid recovery from surgery [3, 6, 18, 19]. Separation surgery in combination with stereotactic radiation has been demonstrated by Laufer et al to provide 1-year local control rates of more than 91% regardless of tumor histology radiosensitivity. [20]

Laser thermal therapy has been used to treat cranial [36, 37], liver[38] and bone[25] lesions. The biggest advantage of this modality is compatibility with magnetic resonance imaging (MRI). As heat is generated in tissue, changes in the magnetic resonance can be translated into a thermal map and overlay of a coplanar anatomic images allow real time monitoring of the intensity and spread of heat in the tissue as the laser is fired [39]. This technology has been used in neurosurgery to treat intracranial metastases [37], primary brain tumors [36] and epilepsy [40] with excellent results and low morbidity. Ahrar and Stafford [25] report the use of laser interstitial thermotherapy (LITT) to treat spinal metastasis, but their study excluded tumors extending to the epidural space. These authors concluded that LITT is a safe and reliable technique, but recognized to the technical challenges in placing the probe inside the tumor, as they used a free hand technique guided by MRI without stereotactic image guidance. This application never achieved large interest, since SSRS provides better accuracy and local control to the tumors selected for the study.

SUMMARY

Placement of spinal instrumentation or needle biopsies are traditionally performed using x-ray fluoroscopy images, which have limitations in identifying the three-dimensional (3D) spinal, bony and soft tissue anatomy especially in cases of osteoporotic bone, severe deformity or morbidly obese patients. Laboratory and clinical studies have demonstrated that utilization of computed tomography (CT)-based image guidance increases the safety and accuracy of a variety of spinal procedures; however, it relies on acquisition of CT images in the operative position requiring expensive dedicated equipment in order to avoid distortion of surface landmarks to obtain accurate registration of the surface landmarks. CT images are suboptimal to identify soft tissue anatomy and some ablative procedures are performed by just placement of the catheter or probe and the lesion occurs by a presumed distribution of heat or cold around the catheter.

Recently, magnetic resonance (MR) thermography has been introduced in combination with interstitial laser to ablate soft tissue. This method has been applied in the liver and brain. Exemplary embodiments of the present disclosure introduce its application to other areas, including the spine, muscle and soft tissue around the spine. However, the placement of the laser catheter is quite difficult. In previous methods, spinal image guidance has been done with pre-procedure CT scans matched with real time fluoroscopic imaging. This method is subject to limitations in obese patients, upper thoracic region due to overlapping of the ribs and scapula, therefore being difficult to have a surface or reliable deep landmark for verification of accuracy in percutaneous procedures.

Exemplary embodiments of the present disclosure constitute the utilization of intraoperative MRI images, acquired with the patient in the operative position. In exemplary embodiments, the surface markers are protected from distortion (related with movement of the skin due to pressure from the MRI coils and other instruments) from the time the MR images are acquired to the time those markers are registered. Once these markers are registered, a method was developed that is based on intraoperative MRI to verify accuracy of the needle or instrument being used to approach the deep seated soft tissue lesion, in order to confirm a safe trajectory to avoid damage to vital organs or structures that could be located close to the target.

Embodiments of this invention describe the utilization of intraoperative image guidance based on MRI to reach deep seated targets, including for example, in the spine, epidural space, paraspinal muscle and visceral organs. This allows placement of the laser ablation catheter in the soft tissue (tumor) and performance of the laser ablation under MR thermography to be performed on the MRI table, avoiding moving the patient from a stretcher into the MRI magnet. It also allows a precise verification of the accuracy of navigation at a safe stage, where if the surgeons feel the parameters are inaccurate, major damage can be avoided.

The utilization of laser ablation to spine tumors can be used for the treatment of deep seated primary or metastatic cancer causing compression of the spinal cord. Exemplary embodiments of the procedure allow a percutaneous alternative to open surgery, which is an advantage since there is less blood loss, less collateral damage to soft tissue, in some cases avoids need for placement of spinal hardware and allows faster recovery and return to cancer treatment with minimal interruption. Exemplary embodiments can complement stereotactic radiation in situations where the dose of radiation has to be decreased to avoid damage of vital organs, like the spinal cord when compressed by tumor.

Exemplary embodiments of the present disclosure include a method for applying thermal energy to a target tissue in a region of interest. In certain embodiments, the method comprises: coupling a plurality of fiducial markers to tissue proximal to the region of interest; obtaining a magnetic resonance image (MRI) of the region of interest; registering the plurality of fiducial markers with a stereotactic image guidance system; verifying surface accuracy of the stereotactic image guidance system; inserting an MRI-compatible instrument into the region of interest; verifying sub-surface accuracy of the stereotactic image guidance system; inserting a laser fiber into the target tissue in the region of interest; applying thermal energy to the target tissue; and monitoring temperature in the target tissue and the region of interest.

In certain embodiments, the MRI compatible instruments are included in a system comprising a two piece sturdy MRI compatible frame, in which the "lower piece" is securely attached to the MRI table, enabling placement of an MRI coil and the appropriate padding for bony prominences under the region of interest of the patient being treated. Exemplary systems can also include an appropriately designed MRI coil compatible with the lower portion of the frame. Exemplary embodiments can also comprise an upper portion of the frame, which can be attached and removed during the surgical procedure. This can allow placement of a second MRI coil held above the fiducial markers, avoiding contact with the dorsal skin and displacement of the fiducials. In exemplary embodiments, the upper MRI coil is configured with a design to allow a working area to provide for registration and manipulation of the navigated surgical instruments above the fiducials. Certain embodiments can also comprise an MRI compatible needle holder, which can be securely attached to the frame and allow stabilization, change in angles, and position in the X, Y and Z coordinates of the navigated access needle as it is advanced towards the target. Particular embodiments can also comprise MRI compatible adaptors in order to add more than one laser catheter in a trajectory within a 5-15 mm distance from the prior trajectory. Specific embodiments may also include an appropriate attachment for a reference array used to register the fiducials and image guidance during the procedure.

Exemplary embodiments of the system would avoid changing patient from operative tables and avoid changes in operative positioning during the procedure. The embodiments would allow obtaining the pre-operative localizatory images of the region of interest with better resolution since it allows MRI scanning with a 360 degree coverage with MRI coils of the cervical/thoracic/abdominal/lumbar/sacral region. Exemplary embodiments of the system can allow intraoperative MR scanning and verification of accuracy when the needle is inserted in the subcutaneous tissue at a safe distance from critical organs (blood vessels, spinal cord, nerves, visceral organs) and allow a controlled advancement and change in direction (X,Y,Z) and angles of approach at discretion of the surgeon. Embodiments of the system can also allow for MRI thermography during the laser ablation with better resolution since the region of interest will be covered with the appropriate MRI coils.

In certain embodiments, the target tissue is a tumor, and in particular embodiments, the region of interest is proximal to a spinal cord. In some embodiments, the region of interest comprises the dura mater. In specific embodiments, coupling the plurality of fiducial markers to tissue proximal to the region of interest comprises applying an adhesive sheet to epidermal tissue. Certain embodiments further comprise removing a portion of the adhesive sheet prior to inserting an MRI-compatible instrument into the region of interest, and in particular embodiments, a portion of the plurality of fiducial markers each comprise an aperture. Some embodiments further comprise marking locations of the apertures on epidermal tissue proximal to the region of interest. In specific embodiments, verifying the surface accuracy of the stereotactic image guidance system comprises touching an instrument to epidermal tissue proximal to the region of interest.

In certain embodiments, the MRI-compatible instrument is a needle comprising a removable trocar. Particular embodiments further comprise removing the removable trocar from the needle and inserting a wire through the needle. Some embodiments further comprise inserting a cannula over the wire, and in specific embodiments, inserting a laser fiber into the target tissue in the region of interest comprises inserting the laser fiber through the cannula.

In certain embodiments, the laser fiber has a diameter of less than 2.0 mm, and in particular embodiments, the laser fiber comprises silica fiber optic wire. In some embodiments, the laser fiber is coupled to a laser generator configured to generate electromagnetic radiation having a wavelength between 600 and 1200 nm, and in specific embodiments, the laser fiber is coupled to a laser generator configured to generate electromagnetic radiation having a wavelength of approximately 980 nm.

In certain embodiments, monitoring temperature in the target tissue and the region of interest comprises an application of magnetic resonance thermography. Particular embodiments further comprise increasing oxygen levels in blood of the patient prior to applying thermal energy to the target tissue. Specific embodiments further comprise holding mechanical ventilation while monitoring temperature in the target tissue and the region of interest. Some embodiments further comprise automatically stopping application of thermal energy to the target tissue if a temperature in the target tissue or a temperature in the region of interest reaches a predetermined value. In certain embodiments, the region of interest is proximal to an eye, and in particular embodiments the region of interest is proximal to a lung.

Exemplary embodiments include a system for imaging and applying thermal energy to a target tissue in a region of interest. In certain embodiments, the system comprises: a sheet comprising fiducial markers; a laser fiber configured to apply thermal energy to the target tissue; a stereotactic image-guidance system configured to register a position of the laser fiber; and a magnetic resonance thermography system configured to monitor a temperature of the target tissue and a temperature of the region of interest.

Particular embodiments further comprise a magnetic resonance imaging (MRI) scanner. In some embodiments, the sheet comprising fiducial markers further comprises: a first side, a second side, and an adhesive applied to the first side; a plurality of apertures, wherein a portion of the fiducial markers each comprise an aperture extending through the sheet; and a removable portion. Specific embodiments further comprise a magnetic resonance imaging (MRI)-compatible needle. In certain embodiments, the magnetic resonance imaging (MRI)-compatible needle comprises a removable trocar. Particular embodiments further comprise a wire configured for insertion through the magnetic resonance imaging (MRI)-compatible needle. In some embodiments, the wire is a Kirschner wire, and specific embodiments further comprise a cannula.

Fiducial markers can be comprised of any piece of material that is compatible with MRI without creating image artifacts, located attached to the skin or to the reference frame, which would allow passive or active registration and tracking for image guidance during the procedure. In this disclosure, passive registration is used to refer to when the surgeon points an MRI compatible instrument recognized by the navigation system, allowing input to a computer software of the position of the each passive fiducial applied to the patient's skin. Active registration would be considered when the navigation software can automatically recognize the position of each active fiducial and the reference array and elaborate the appropriate parameters for image guidance without any contact to the patient.

Exemplary embodiments include an apparatus for applying fiducial markers to a patient. In certain embodiments, the apparatus comprises: a sheet comprising a first side, a second side, and a detachable portion; an adhesive applied to the first side of the sheet; and a plurality of fiducial markers coupled to the second side of the sheet, wherein a portion of the plurality of fiducial markers each comprise an aperture extending through the fiducial marker. In particular embodiments, the plurality of fiducial markers comprises a plurality of reference markers and a plurality of registration markers. In some embodiments, the plurality of registration markers each comprise an aperture. Specific embodiments further comprise a detachable portion. In certain embodiments, the detachable portion is configured to be removed from a central portion of the apparatus. In particular embodiments, the apparatus is configured to surround an opening created when the detachable portion is removed from the apparatus. Some embodiments further comprise a sterile drape covering the opening.

Certain embodiments include a system for imaging a target tissue in a region of interest, where the system comprises: a magnetic resonance imaging (MRI)-compatible frame comprising a lower portion and a detachable upper portion; a lower magnetic resonance imaging (MRI) coil coupled to the lower portion of the magnetic resonance imaging (MRI)-compatible frame; and an upper magnetic resonance imaging (MRI) coil coupled to the upper portion of the magnetic resonance imaging (MRI)-compatible frame, wherein the upper magnetic resonance imaging (MRI) coil comprises a central opening.

In particular embodiments, the central opening is configured to provide access to a plurality of fiducial markers coupled to a patient positioned between the lower magnetic resonance imaging (MRI) coil and the upper magnetic resonance imaging (MRI) coil. In some embodiments, the central opening is configured to allow for registration and manipulation of surgical instruments above the plurality of fiducial markers. In specific embodiments, the upper portion of the magnetic resonance imaging (MRI)-compatible frame comprises an attachment configured to position an array of reference markers. Certain embodiments further comprise an instrument holder configured to couple to a magnetic resonance imaging (MRI)-compatible frame. In some embodiments, the instrument holder comprises a first joint configured to allow movement in an X-Y plane. In specific embodiments, the instrument holder comprises a second joint configured to allow movement in a Z-direction perpendicular to the X-Y plane. In particular embodiments, the instrument holder comprises an adapter configured to couple retain multiple instruments. In certain embodiments, the adapter is configured to retain multiple instruments at different trajectories.

In the following, the term "coupled" is defined as connected, although not necessarily directly, and not necessarily mechanically.

The use of the word "a" or "an" when used in conjunction with the term "comprising" in the claims and/or the specification may mean "one," but it is also consistent with the meaning of "one or more" or "at least one." The terms "about", "substantially" and "approximately" mean, in general, the stated value plus or minus 5%. The use of the term "or" in the claims is used to mean "and/or" unless explicitly indicated to refer to alternatives only or the alternative are mutually exclusive, although the disclosure supports a definition that refers to only alternatives and "and/or."

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements, possesses those one or more steps or elements, but is not limited to possessing only those one or more elements. Likewise, a step of a method or an element of a device that "comprises," "has," "includes" or "contains" one or more features, possesses those one or more features, but is not limited to possessing only those one or more features. Furthermore, a device or structure that is configured in a certain way is configured in at least that way, but may also be configured in ways that are not listed.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will be apparent to those skilled in the art from this detailed description.

DETAILED DESCRIPTION OF ILLUSTRATIVE EMBODIMENTS

Figure 1:
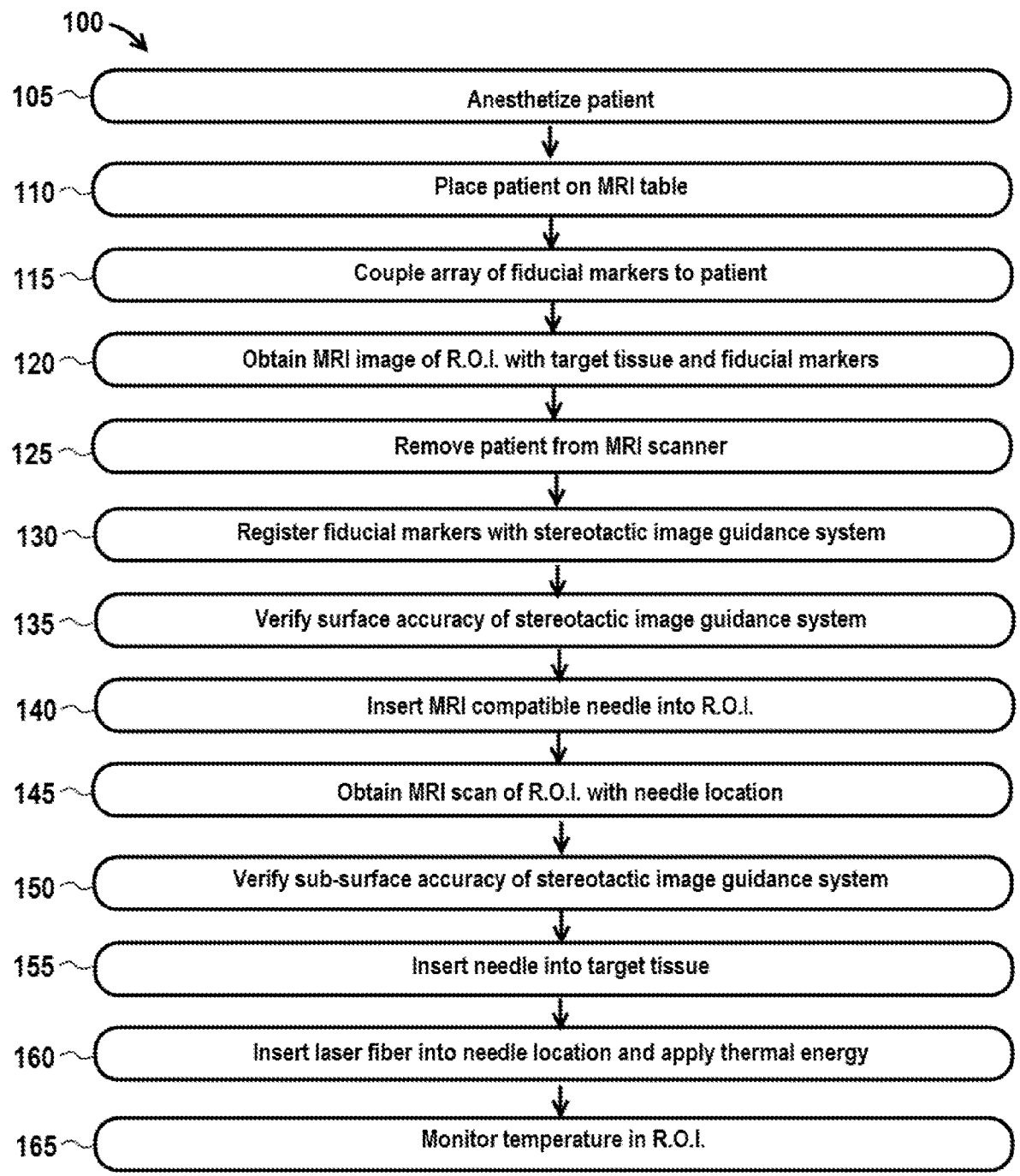
FIG. 1 displays a flowchart of an exemplary method according to the present disclosure.

Referring initially to FIG. 1, a flowchart illustrates an overview of steps in one exemplary method 100 of the present disclosure. It is understood that some exemplary methods may not comprise each of the steps listed in FIG. 1, while other exemplary methods may comprise additional steps not listed in FIG. 1. In method 100, a patient is anesthetized as provided in step 105. The patient can then be placed on an MRI table in step 110, and an MRI compatible array of reference and fiducial markers can be coupled to the patient in step 115. In exemplary embodiments, the array of reference and fiducial markers can be coupled to the patient via an adhesive sheet. The reference and the fiducial markers may or may not be combined in a single unit and coupled to the patient to tissue (e.g. epidermal tissue) proximal to a region of interest (e.g. a region of the patient in which treatment or further analysis will be performed).

An MRI image can then be obtained of the region of interest and the fiducial markers in step 120. For example, a radiofrequency (RF) coil can be placed around the region of interest and the fiducial markers, and an MRI scan performed of the region of interest (ROI) and fiducial markers by an MRI scanner. In step 125, the patient can be removed from the MRI scanner and the RF coil removed. The fiducial markers can then be registered with a stereotactic image guidance system in step 130. In particular embodiments, the fiducial markers can be registered in a stereotactic image guidance system by directing a navigation camera at the fiducial markers and placing a probe that contacts the patient's epidermis in a hole located in the center of the fiducial marker. In specific embodiments, the fiducial markers can be registered via the Softouch® registration system available from Brainlab AG. Alternatively, the fiducial markers can be recognized by the navigation software just by pointing the camera in the region of interest containing the fiducials and automatic touchless registration obtained as happens in the TREGS, BrainSuite® system available from Brainlab AG. In step 135, the surface accuracy of the stereotactic image guidance system can then be verified by touching the surface of the skin and comparing the actual location with the location indicated by the image guidance system.

After verification of the stereotactic image guidance system at the skin surface, an MRI compatible needle can be inserted into the patient proximal to the region of interest in step 140. In specific embodiments, the needle can be inserted to a particular safe location (e.g. in contact with the lamina, spinous process or a vertebral body), and a sterile drape placed over the needle incision. In step 145, the patient can be placed into the MRI scanner and an MRI scan can be performed of the region including the needle to obtain an image showing the actual location of the needle. The patient can then be removed from the MRI scanner, and the actual position of the needle shown in the MRI scan can be compared either by subjective impression by the surgeon, or by a computer algorithm to identify inaccuracy of the predicted position of the needle indicated by the image guidance system in step 150 to verify sub-surface accuracy of the stereotactic image guidance system (e.g. accuracy of images below the surface of the patient epidermis).

Once the sub-surface accuracy of the image guidance system is established, the needle can be inserted into the target tissue (e.g. a tumor) in step 155. The location of the needle in the target tissue can be monitored and verified with the image guidance system. In specific embodiments, the needle inserted into the target tissue comprises a removable central trocar, and in particular embodiments, the needle may be a Jamshidi® needle. A laser fiber can be inserted into the needle location and thermal energy can be applied to the target tissue in step 160. For example, a central trocar can be removed from the needle and a laser inserted into the location of the needle. In particular embodiments, a central trocar can be removed and a Kirschner wire (also known as a K-wire) inserted through the needle, which can then be removed. The K-wire can then be used as a guide for placement of a non-ferromagnetic plastic access cannula, and a laser fiber inserted through the cannula in specific embodiments. The laser fiber can then be activated to apply thermal energy and increase the temperature to the target tissue.

The temperature of the tissue in the region of interest (including for example, the target tissue and the surrounding tissue) can be monitored in step 165. In certain embodiments, MR thermography can be used to monitor the temperature, and in particular embodiments, the temperature is monitored by phase-difference imaging with gradient-echo acquisition as described by Ahrar and Stafford [25].

In exemplary embodiments, thermal energy is applied to the target tissue sufficient to raise the temperature to a level sufficient to provide the desired therapy to the target tissue while minimizing the effects of tissue surrounding the target tissue. In particular embodiments, the target tissue may be a tumor proximal to a patient's spinal cord. In such embodiments, thermal energy can be applied to the tumor at a level sufficient to ablate the tumor without raising the temperature of surrounding tissue beyond a desired level. In certain embodiments, the temperature monitoring system may include an automatic shut off that stops the application of thermal energy to the target tissue if the temperature of the surrounding tissue exceeds a certain value. For example, in applications to ablate tumors proximal to the spinal cord, the temperature of the interface between an epidural tumor and the dura mater can be monitored to verify the interface temperature does not exceed 50 degrees Celsius. If the interface temperature reaches this threshold, the temperature monitoring system can stop the application of thermal energy to the target tissue (e.g. by deactivating the laser fiber inserted into the tumor).

In exemplary embodiments of the present disclosure, motion of the patient can affect the accuracy of the thermal monitoring. In certain embodiments, mechanical ventilation is held during the acquisition of the parameters and during the application of thermal energy. In such embodiments, users can pre-oxygenate the patient (e.g. to an $SpO_2$ of 100%) before holding mechanical ventilation. Capnography curves can be used to track ventilatory movements. Once the curve shows apnea, the laser fiber can be activated (e.g. at 65 to 70% of the 30 W of potency with a maximum pause in ventilation of 100 seconds).

At this point ventilation can be resumed and the laser fiber withdrawn 5 mm. This cycle can be repeated multiple times to ensure adequate thermal coverage before switching the laser fiber to another access cannula (if multiple cannulas are utilized to apply thermal energy to the target tissue). The procedure can be interrupted and ventilation immediately resumed if $SpO_2$ falls below 94% or if the temperature reaches the predefined temperature threshold proximal to the spinal cord (automatic deactivation).

Figure 2:
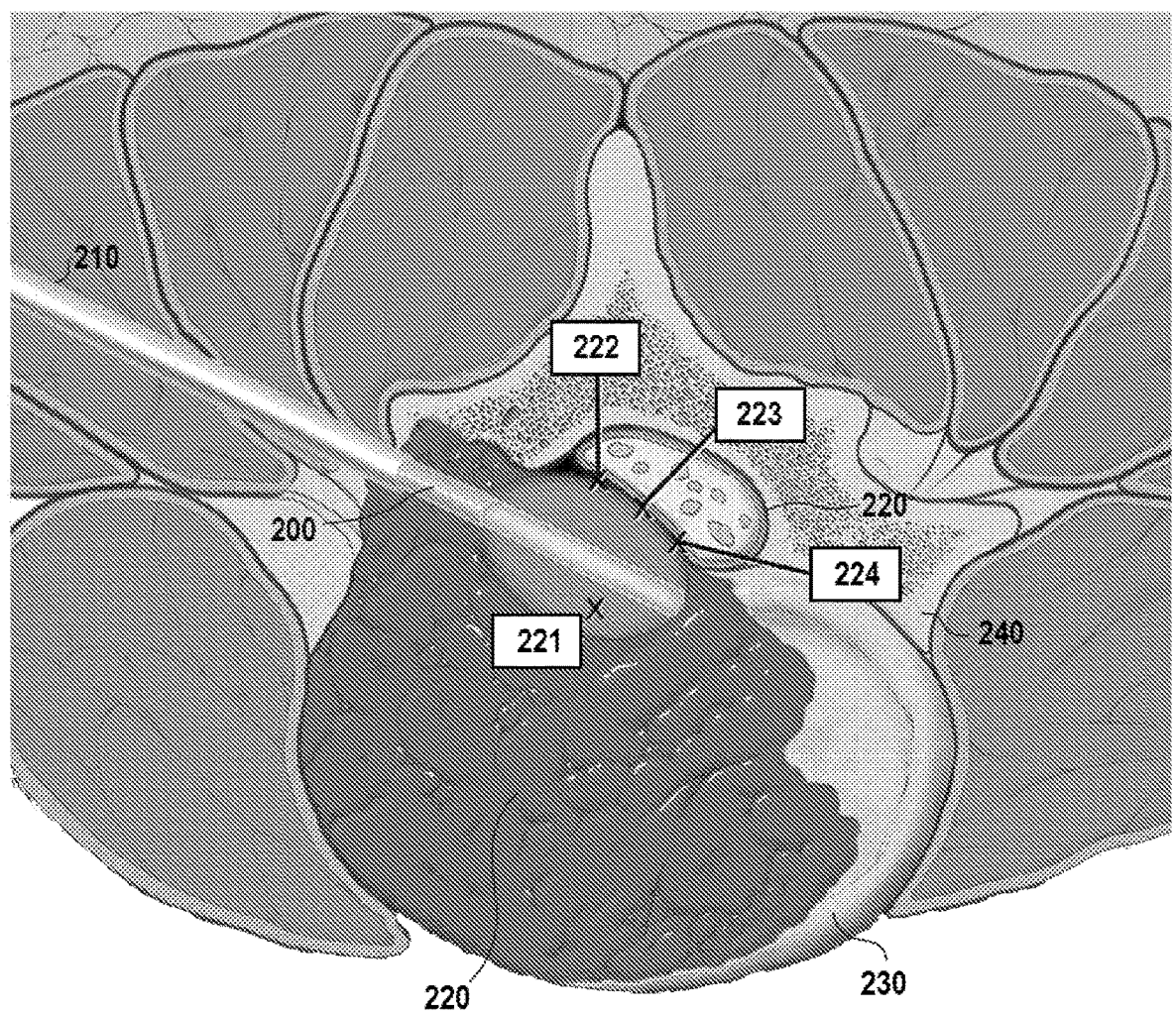
FIG. 2 displays a cross-section view a target tissue and region of interest during a procedure according to the present disclosure.

Referring now to FIG. 2, a cross section view is shown of an embodiment applying thermal energy to tumor proximal to a spinal cord. In this embodiment, a laser fiber 200 is inserted through a cannula 210 (e.g. according to methods described above in the discussion of FIG. 1). Laser fiber 200 can be activated to apply thermal energy to a target tissue 220, which in this embodiment is a tumor proximal to a spinal cord 230 and vertebra 240. During operation of laser fiber 200, the temperature of multiple locations in target tissue 220 and proximal to target tissue 220 can be measured. For example, the temperature of target tissue can be measured at location 221, while the temperature at locations 222, 223 and 224 of the interface between target tissue 220 and dura mater 250 can also be monitored.

In the embodiment shown in FIG. 2, the temperature at location 221 can be monitored to verify the temperature is raised to a level sufficient to ablate tissue in target tissue 220. In particular embodiments, this temperature may be in a range of 50-100 degrees Celsius, or more particularly 60-90 degrees Celsius, or still more particularly 70-80 degrees Celsius. In addition the temperature of locations 222, 223 and 224 can be monitored to verify the temperature is not raised to a level high enough to damage tissue proximal to target tissue 220 (e.g. tissue in dura meter 220). In specific embodiments, the temperature at locations 222, 223, and 224 can be monitored to verify it does not exceed a particular threshold, including for example, 50 degrees Celsius. It is understood that the locations shown in FIG. 2 are merely exemplary, and that embodiments of the present disclosure can be configured to monitor tissue in additional locations. In particular embodiments, an MR thermography system can be used to monitor temperatures at locations based on individual pixels in the display. In specific embodiments, upper temperature limits can be set for multiple locations so that laser 200 is automatically deactivated if an upper temperature limit is reached.

Figure 3:
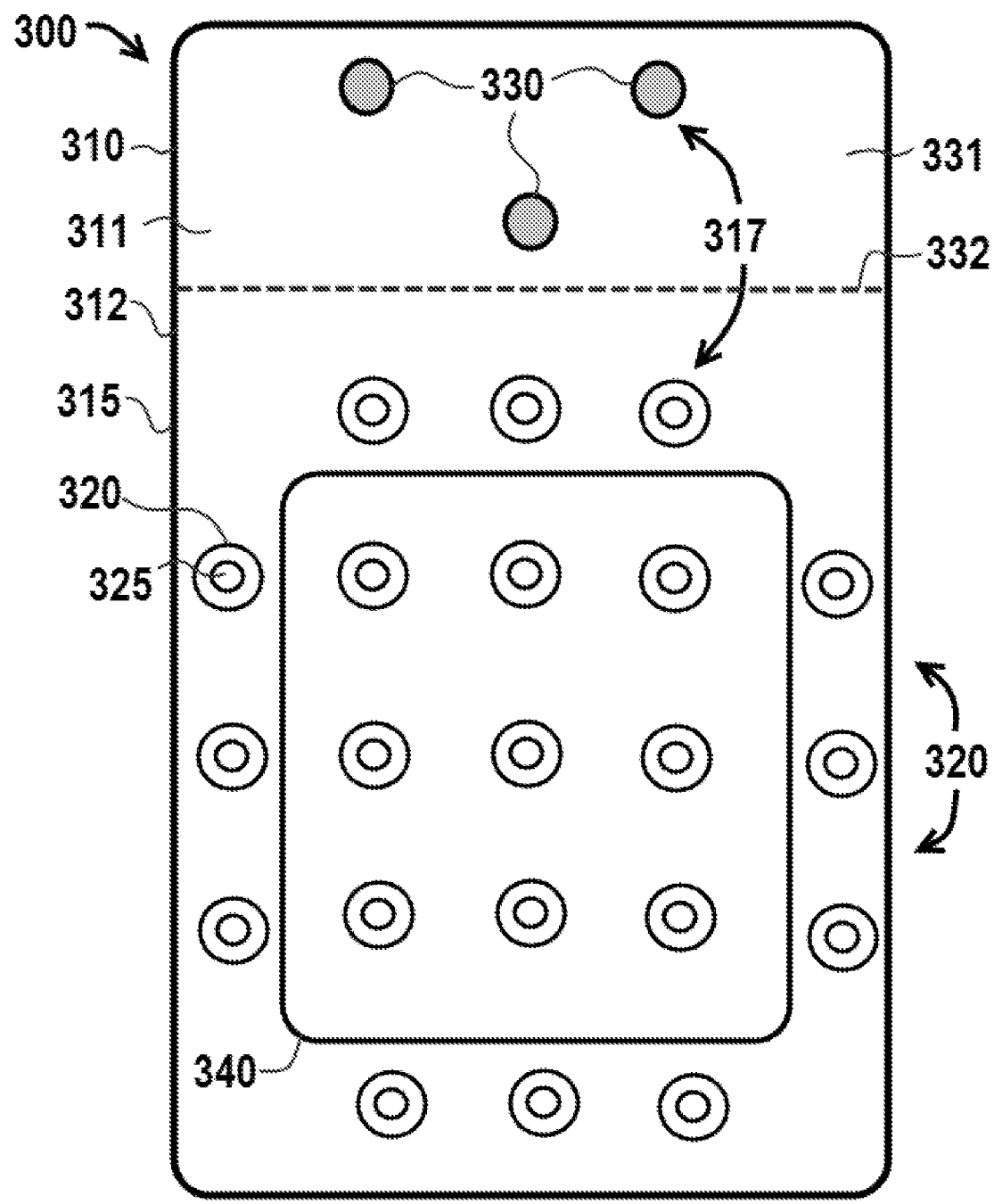
FIG. 3 displays a top view of an apparatus comprising fiducial markers according to the present disclosure.

Referring now to FIG. 3, a top view of apparatus 300 is shown. Apparatus 300 can be used in exemplary embodiments to couple fiducial markers to a patient. In the embodiment shown, apparatus 300 comprises a sheet 310 comprising a first side 311 and a second side 312. In this embodiment, side 312 comprises an adhesive 315 that can allow apparatus 300 to be coupled to a patient. Side 311 comprises an array of fiducial markers 317, including reference markers 330 (which can be detached along line 332 and placed as a separate unit 331 according to surgeon's preference) and verification markers 320. In the embodiment shown, verification markers 320 each comprise an aperture 325 extending through markers 320 and apparatus 300. In this embodiment, apparatus 300 also comprises a detachable portion 340, which can be removed from a central area of apparatus 300 such that the remaining portion of apparatus 300 surrounds an opening created by removal of detachable portion 340.

In certain embodiments, adhesive 315 is applied to the patient's skin in the desired location to couple the array of fiducial markers 317 to the patient. For example, detachable portion 340 can be located over the area of the skin into which instruments [e.g. needle(s), cannula(s), K-wire(s), and/or laser fiber(s)] will be inserted to target tissue as described in the discussion of the method provided in FIG. 1. As previously described, the fiducial markers can be registered with a stereotactic image guidance system to ensure accurate positioning of instruments used to apply thermal energy to target tissue. In particular embodiments, a registration instrument (including for example, a Softouch® instrument) can be placed in one or more apertures 325 of verification markers 320 and touched to the patient's skin. Alternatively, the fiducial markers can be automatically recognized by the navigation system and touchless registration achieved by just pointing the camera to the fiducials (including for example the TREGS and the Brainsuite® head coil).

In specific embodiments, detachable portion 340 can be removed from apparatus 300 after the location of fiducial markers 317 has been registered. This can allow a user to access an area of tissue above the region of interest and target tissue, which is covered by the built in sterile adhesive drape. In particular aspects, the built in sterile drape can cover the area of tissue exposed by the removal of portion 340. In specific embodiments, the sterile drape can be an Ioban™ available from 3M.

Another embodiment of the present disclosure incorporates the use of MRI-compatible navigation hardware. Such hardware may include, for example, a reference array, navigation probe, registration probe, and any other components or apparatus that use image guidance and can be coupled to the MRI table or patient (e.g. a mechanical arm for stereotactic frameless navigation, spinous process clamp or iliac crest fixation devices). The navigation hardware can be made MRI-compatible by excluding ferromagnetic materials and using non-ferromagnetic materials in the construction of the hardware. Such non-ferromagnetic materials include a metal alloy (titanium or aluminum) or a plastic [polyether ether ketone (PEEK) or acrylic].

Such embodiments can avoid manipulation of the patient's skin after an MRI scan is conducted. For example, a surgeon can couple a standard reference array to a fixed location on the patient (e.g. with a spinous process clamp in embodiments applying therapy to target tissue proximal to the spine) prior to the placement of fiducial markers. The surgeon can then obtain an MRI image of target the region of interest and the reference array and remove the patient from the MRI scanner. The surgeon can then register the fiducial markers and proceed with inserting a laser fiber into the target tissue while monitoring the position of the laser fiber with the stereotactic image guidance system. When the laser fiber is located in the desired position, thermal energy can be applied to the target tissue, and MR thermography can be used to monitor the temperature of the target tissue and surrounding tissue in the region of interest.

Figure 4:
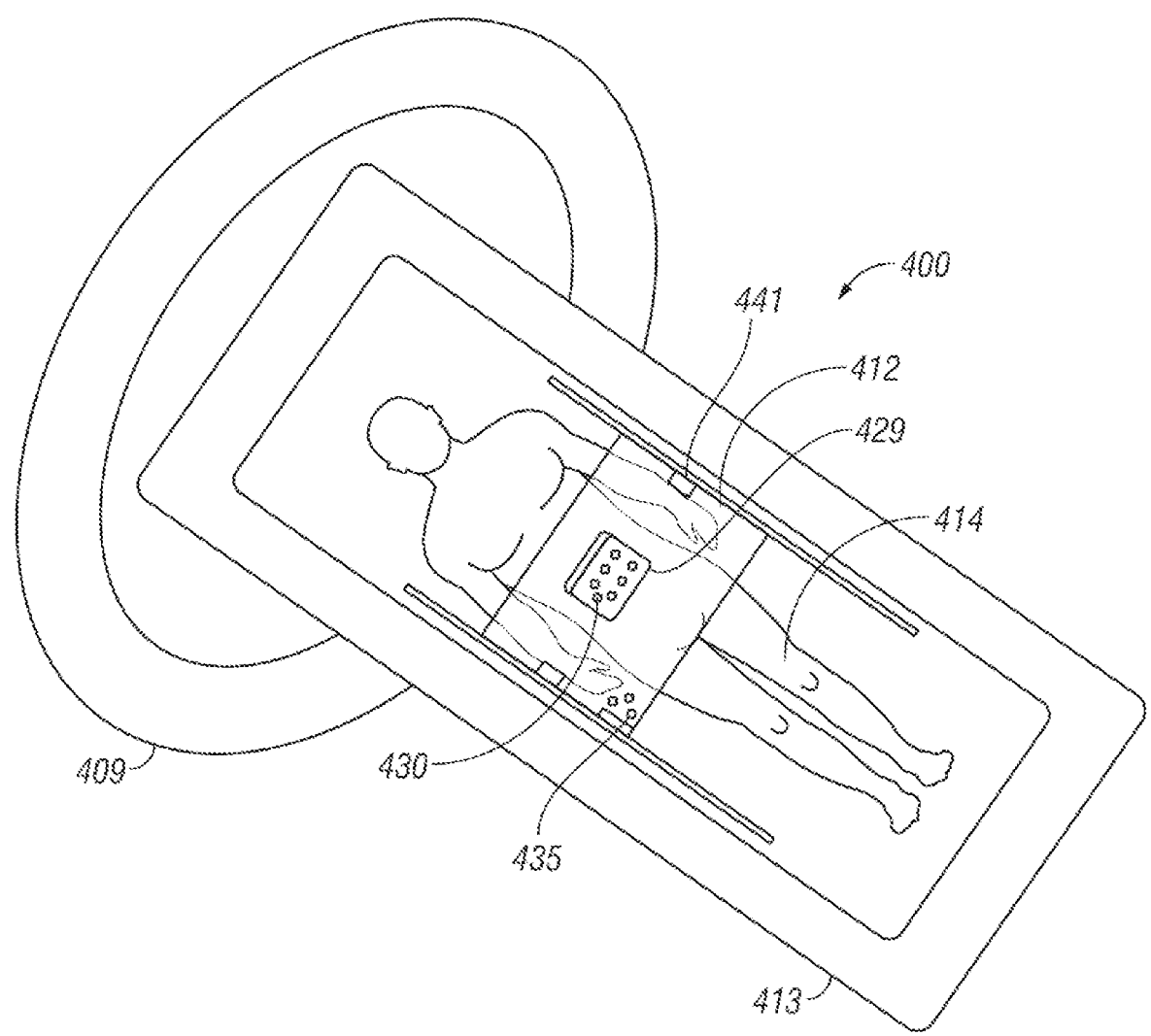
FIG. 4 displays a top view of an imaging an instrument guidance system.
Figure 5:
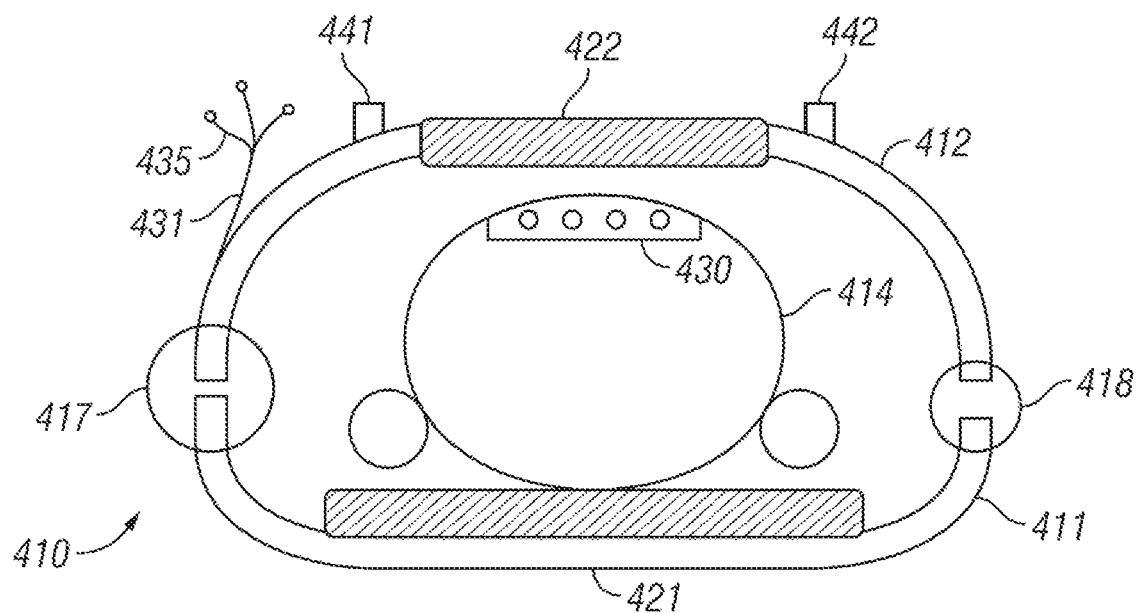
FIG. 5 displays an end view of the system of FIG. 4.

Referring now to FIGS. 4 and 5, in certain embodiments system 400 may include an MRI-compatible frame 410 comprising a lower portion 411 and an upper portion 412. In this embodiment, lower portion 411 is securely attached to an MRI table 413 (shown proximal to MRI magnet 409), enabling placement of an MRI coil 420 and the appropriate padding for bony prominences under the region of interest of a patient 414 being treated. In the illustrated embodiment, MRI coil 420 comprises a lower coil 421 (compatible with frame lower portion 411) and an upper coil 422 (compatible with frame upper portion 412). Frame upper portion 412 can be coupled to lower portion 411 (at coupling locations 417 and 418) and then removed during the surgical procedure. This can allow placement of an upper coil 422 such that it is held above fiducial markers 430, avoiding contact with the dorsal skin and displacement of fiducial markers 430. In certain embodiments, upper coil 422 can be configured to allow a working area with an opening 429 for registration and manipulation of the navigated surgical instruments above fiducial markers 430.

Figure 6:
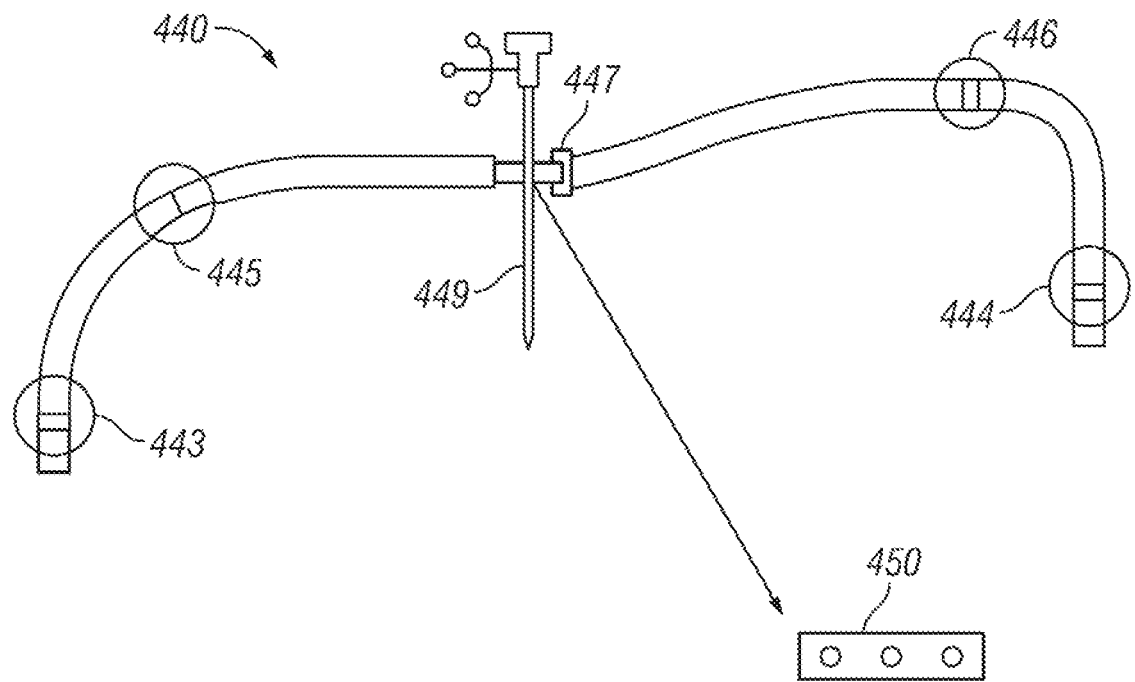
FIG. 6 displays a side view of an instrument holder configured for use with the system of FIG. 4.

Exemplary embodiments may comprise an attachment 431 for positioning an array 435 of reference makers used to register fiducial markers 430 and provide image guidance during the procedure. Certain embodiments may also comprise coupling locations 441 and 442 for an instrument holder 440 (e.g. a device configured to hold a needle or other instrument as shown in FIG. 6) that is MRI compatible. During use, instrument holder 440 can be securely attached to frame 410 via coupling locations 443 and 444. This can allow stabilization as well as change in angles and position in the X, Y and Z coordinates of a navigated access needle 449 as it is advanced towards the target. In the illustrated embodiment, an instrument holder 440 comprises a plurality of joints 445 and 446 that allow movement in the X-Y plane and a joint 447 that allows movement in the Z-direction. It is understood that other embodiments may comprise a different configuration to allow movement in the X, Y and Z planes. In addition, instrument holder 440 may comprise one or more adapters 450 configured to add more than one laser catheter in a trajectory within a 5-15 mm distance from the prior trajectory.

Exemplary embodiments of the system would avoid changing patient from operative tables and avoid changes in operative positioning during the procedure. The exemplary embodiments would also allow obtaining the pre-operative localizatory images of the region of interest with better resolution since it allows MRI scanning with a 360 degree coverage with MRI coils of the cervical/thoracic/abdominal/lumbar/sacral region. Disclosed embodiments can further allow intraoperative MR scanning and verification of accuracy when the needle is inserted in the subcutaneous tissue at a safe distance from critical organs (e.g. blood vessels, spinal cord, nerves, visceral organs). Furthermore, exemplary embodiments can allow a controlled advancement and change in direction (e.g. in the X, Y, Z coordinate) and angles of approach at discretion of the surgeon. The disclosed embodiments can also allow perform MRI thermography during the laser ablation with better resolution since the region of interest will be covered with the appropriate MRI coils.

A working example of one embodiment of the present disclosure is provided below. It is understood that the scope of the present disclosure is not limited by the example provided, and that other embodiments within the scope of this disclosure may comprise additional, fewer, or different aspects than those described in this working example.

Working Example

High grade malignant spinal cord compression is commonly managed with a combination of surgery, aiming removal of the epidural tumor, followed by stereotactic spinal radiosurgery (SSRS), aiming local tumor control. The investigators introduce the use of spinal laser interstitial thermotherapy (SLITT) as an alternative to surgery prior to SSRS.

Eleven patients with high degree of epidural malignant compression due to radio-resistant tumors were selected. Visual analog pain score (VAS) and quality of life score (QoL) were obtained before, within 30 and within 60 days after the procedure. The investigators performed percutaneous placement of a laser probe in the epidural space. Real time thermal MR was used to monitor the tissue damage in the region of interest. All patients received post-op SSRS. The maximum thickness of the epidural tumor was measured and the degree of the epidural spinal cord compression (ESCC) scored in pre and post procedure MRI as follows: Grade 0: tumor contained inside the vertebral body; Grade 1: tumor extending to the epidural space without displacement of the dura; Grade 2: tumor compressing the dura, without touching the spinal cord; Grade 3: tumor compressing the dura, touching the spinal cord; Grade 4: tumor compressing and displacing the spinal cord, but with CSF visible posterior to the cord; and finally Grade 5: epidural compression with complete obliteration of the CSF space.

Results: Mean VAS for pain was 6.18; 4.27; 2.8 and median VAS for quality of life was 60%; 70%; 70% respectively at pre-op, within 30, and 60 days after treatment. Image follow up 2 months after the procedure demonstrated significant reduction in the mean thickness of the epidural tumor from 8.82 mm (95% CI 7.38-10.25) pre-treatment to 6.36 mm (95% CI 4.65-8.07) after SLITT and SSRS (p=0.0001). The median pre-operative ESCC score was 4 (range 2-5), which was significantly higher than the score of 2 (range 1-5), (p=0.04) on imaging follow up 2 months after the procedure.

Conclusion: The investigators present the first report of an innovative minimally invasive alternative to the management of spinal metastasis; in early experience it provided local control with low morbidity and improvement in pain and quality of life of patients.

Introduction

Over the last 40 years, significant progress has been made in the management of metastatic disease causing spinal cord compression. In the 1980's, laminectomy for posterior decompression plus radiotherapy was shown to worsen pain and neurological function compared to radiotherapy alone [1, 2]. In this context, conventional external beam radiation therapy (cEBRT), which was able to provide a similar or better outcome with less morbidity, became the standard of care [1-4]. Unfortunately, radio-resistant histologies demonstrated less than favorable responses [5],[6] with a significant subset of patients deriving little palliative benefit or tumor control from this modality alone [7, 8]. In subsequent years better understanding of spinal biomechanics and the development of internal spinal fixation revitalized the role of surgery in the management of spinal metastasis, resulting in improved functional outcome and local control. A randomized controlled trial [9], demonstrated the superiority of circumferential decompression and stabilization surgery followed by cEBRT in maintaining and recovery of ambulation, maintenance of continence, pain control, and functional performance when compared to cEBRT alone.

A better understanding of radiobiology and technological advancements in image guidance over the last decade allowed the development of stereotactic body radiotherapy (SBRT), in which radiation is contoured to cover a specific target volume, with a steep fall-off in radiation delivered to surrounding tissues, limiting the toxicity to organs in proximity to the tumor [10, 11]. The delivery of high doses of radiation in single-dose [12] or hypofractionated regimens has been shown to overcome the radio-resistance of certain histologies to fractionated cEBRT[11-14]. SBRT has become an effective tool in the management of spinal metastasis[15, 16]. Unfortunately, despite the highly contoured nature of radiation dose delivery, the fall-off of radiation dosing is not absolute. In the case of epidural disease displacing the spinal cord, the dose of radiation has to be decreased in the region adjacent to the spinal cord, which may result in failure to attain tumoricidal radiation dosing in the epidural compartment and could result in treatment failure [17]. The judicious use of cEBRT, surgery, and SBRT optimized to minimize morbidity in the management of malignant spinal cord compression was popularized by Bilsky et al. [3] in their proposed NOMS framework [6]. These authors coined the term "separation surgery" to describe an operation intended to stabilize the spine and remove the epidural tumor component adjacent to the dura, rather than aiming for a gross total intralesional resection. Once the patient recovers from surgery, SBRT contoured to the original tumor is performed, the epidural disease likely to be underdosed having been managed surgically [3, 6, 18, 19]. Using this approach, Laufer et al. reported 91% local control when separation surgery was used in combination with single-dose SBRT (24 Gy) and 94% local-control when used with high-dose, hypofractionated SBRT (27 Gy divided in 3 fractions) [20].

Percutaneous procedures for tumor ablation are widely used with the intent of local tumor control, as in the treatment of visceral [21, 22] and bone metastasis [23]. In these cases imaging modalities are used to implant a heating or cooling probe into a tumor. The damage created, however, is not monitored and occurs in an assumed but unverified distribution around the tip of the probe. Previously, the utilization of such techniques in the spine has been limited to lesions without significant extension to the epidural space—the prospect of creating unmonitored thermal damage adjacent to the spinal cord being a limiting factor [24, 25]. This application has not gained popularity, as the lesions were more suitable SBRT, which avoids the risk of damage to the neural structures.

An ideal minimally invasive surgical approach to treat spinal metastasis should achieve local tumor control, allow for fast recovery, minimize post-operative pain and morbidity, and curtail delays in initiating or interrupting systemic therapies directed at the primary tumor. Here, the investigators report the utilization of spinal laser interstitial thermotherapy (SLITT) as to be used as an alternative to separation surgery. Our method involves placement of a laser probe under CT based image guidance adjacent to the epidural tumor compartment at an approximated distance of 6 mm from the dural edge. The heating process is monitored in real time by thermal MRI images and once the temperature reaches a critical level at the dural edge, the system deactivates, protecting the spinal cord from thermal damage. This procedure, as with separation surgery, is followed by SBRT in standard doses to cover the gross tumor volume, as if no thermal ablation has been performed. If spinal instability is suspected, percutaneous placement of spinal instrumentation can be performed at the same time and cement augmentation in a second stage. Herein the investigators report our initial findings with this treatment paradigm, where most patients had a short hospital stay, pain scores improved rapidly, interruptions in systemic treatment were avoided and short term local control was achieved.

Methods

Patient Population and Evaluation

This single institution retrospective analysis was reviewed and approved by the MD Anderson Cancer Center institutional review board. All patients had documented spinal metastasis from histologies considered to have unfavorable response to cEBRT. The epidural extension of the tumor was scored based on pre-operative MRI on axial T2 or post-contrast sequences according to the method described by Bilsky et al. [26] Spinal stability was assessed by using the spine instability neoplastic scale (SINS score) as described by Fisher et al. [27]. All cases were presented in a multidisciplinary tumor board conference with neurosurgery, radiation oncology, and radiology, during which consensus was reached that separation of the tumor from the dura prior to SBRT was required in order to reduce the risk of epidural failure. All patients were evaluated with physical exam and had visual analog score for pain and quality of life score collected prior to the treatment, within 30 and 60 days after treatment, and all subsequent follow-up visits (in general every 3 months). Informed consent was obtained in all patients according to institutional policies. All patients underwent post-operative imaging with MRI with contrast at 8 weeks post-procedure. Time between SLITT and the commencement of SBRT, hospital stay, post-ablation complications, and subjective patient satisfaction was recorded.

Pre-Operative Evaluation and Classification of the Status of Systemic Disease

All patients were monitored clinically and systemic radiographic evaluations were performed every 3 to 4 months to restage and evaluate treatment effectiveness or need for change in therapy. The investigators reviewed all imaging studies, including: bone scans, CT scans of the chest, abdomen and pelvis and MRI and CT scans of the spine. The extra-spinal disease was classified as 1) concurrent: when metastatic disease was identified within 30 days of the diagnosis of the spinal tumor and 2) progressing: when there was enlargement or increase in number of lesions on two consecutive imaging studies prior to the laser ablation and 3) stable: when no enlargement or increase in number of lesions was observed on two consecutive imaging studies prior to the procedure.

Stereotactic Placement of the Laser Probe in the Epidural Space

The procedure is performed in the intraoperative MRI (iMRI) (BrainLab Inc., Feldkirchen, Germany) which has a semi sterile preparation room with laminar flow and positive air pressure and fulfills the institutional requirements to allow the performance of percutaneous surgical procedures. After general endotracheal anesthesia is induced, standard antibiotic prophylaxis and a dose of 10 mg of dexamethasone are given and maintained for 12 hrs. The patient is positioned prone over gel rolls placed in parallel along the patient body axis with the arms tucked to the side. The investigators use the iMRI transfer table, which is radiolucent. The investigators place the patient over gel rolls to position the spine in a higher level than the arms allowing clear lateral fluoroscopic images from T3 to the sacrum without interference from the upper extremity skeleton. A C-arm (Siemens, Germany) is connected to the navigation system (BrainLab Inc., Feldkirchen, Germany). The spinous process immediately above the vertebral body of interest is identified and under sterile conditions a small midline incision is performed to expose the tip the selected spinous process. A spinous process clamp is securely attached and a registration array is positioned away from the entry point selected for insertion of the laser probe. A pre-operative CT scan of the spine obtained with a standard navigation protocol is matched to AP and lateral fluoroscopic images of the vertebra attached to the registration array, allowing the navigation system to calculate its parameters for automatic registration. Since the investigators do not have exposure of the deep bony structures, the investigators check accuracy of the registration on the surface of the exposed spinous process under the clamp. Once acceptable accuracy is achieved, the investigators set a posterior lateral transpedicular trajectory to reach a target located at distance of 5 mm from the ventral dural border in the midline of the posterior vertebral body. The investigators use a Jamshidi needle (Codman-Synthes) registered to the stereotactic navigation system, which allows real time image guidance. The needle is advanced through the soft tissues until it reaches the lamina of the vertebral body affected by tumor. If the lateral projection of the navigation is compatible with the tactile sensation of needle touching bone, the needle is moved to the lateral and medial projection of the pedicle wall and its location is confirmed with anterior-posterior (AP) fluoroscopic images. Next, the Jamshidi needle is advanced into the pedicle until it reaches its medial wall. At this stage, the needle should be entering the epidural space and confirmation and comparison with AP fluoroscopic images is performed (FIG. 7), if accuracy is satisfactory, the needle is advanced to the predefined target. At this stage, the investigators remove the central trocar, place a K-wire through the Jamshidi needle, which is subsequently removed, and use the K-wire as a guide for placement of a non-ferromagnetic plastic access cannula.

A distance of 5 mm each side of the laser fiber is covered by temperatures associated with tumor cell death. If more coverage is needed, more access cannulas are placed in tandem with similar technique in order to cover the craniocaudal epidural tumor extension. Lastly, the spinous process clamp is removed and an MRI-compatible titanium needle is inserted into the access cannula and docked into the residual bone of the vertebral body and a sterile plastic bag is used to cover the needles.

The thermal images require the use of surface coils placed over the area of interest. The investigators use two standard Siemens body matrix coils placed on each side of the patient's back, overlapping in the center and held by straps. The body matrix opening of 10×10 cm is positioned so there is easy access to the plastic bag covering the sterile needles. The patient is placed into the MRI magnet and a fast T2 HASTE sequence is used to localize the artifacts of the titanium needles, which allows final confirmation of their trajectory and definition of the exact anatomical plane which will be used for the anatomical and thermal sequences (FIG. 5). The exact coordinates of the first needle are stored, the MRI table is backed out of the magnet, the plastic bag is opened, and the first titanium needle is replaced with the laser fiber, until it reaches the end of the access cannula, which is pulled back over the fiber for 4 cm in order to uncover the tip of the laser probe inside the tumor. During this procedure, blood loss is generally minimal, even in highly vascular lesions such as renal cell carcinoma.

Real Time Monitoring of Heat by Thermal MRI and Thermal Ablation

The laser system (Visualase Inc., Houston, Tex.) is comprised of a computer workstation, a 30 W 980-nm diode laser generator, a cooling pump and a laser applicator set composed of a 400-nm core silica fiber optic with a cylindrical diffusing tip housed within a 1.65-mm diameter saline cooled polycarbonate catheter.

The investigators utilize the imaging process described by Ahrar and Stafford[25]. In brief, heating is monitored by phase-difference imaging with gradient-echo acquisition. The temperature sensitivity of the proton resonance frequency is used to convert changes in phase to estimated changes in tissue temperature on a pixel-by-pixel basis. The investigators use a TR of 38 ms and a flip angle of 20 degrees. The acquisition matrix is 256×128 over fields of view of 24 to 32 cm, typically with a single 3-mm slice being acquired every 5-6 seconds, generating a magnitude and phase image, which are read in real time by the treatment workstation. The extracted information is calculated based on an Arrhenius model and depicted in a color-coded thermal and damage model, which is overlaid with anatomical coplanar T2 images. The software allows monitoring of the temperature in individual pixels. The investigators usually select the pixels in the interface between the epidural tumor and the dura mater (FIG. 6) and set an upper limit of 50° C., if this temperature is reached, the system automatically deactivates, avoiding thermal damage to the spinal cord and nerve roots.

The investigators observed that any motion significantly deteriorates the thermal map and thus the reliability of the method. In order to overcome this problem, mechanical ventilation is held during the acquisition of the parameters and during the thermal damage. The investigators pre-oxygenate the patient to an $SpO_2$ of 100% before holding mechanical ventilation. The investigators use capnography curves to track ventilatory movements. Once the curve shows apnea, the investigators activate the laser fiber at 65 to 70% of the 30 W of potency with a maximum pause in ventilation of 100 seconds. At this point ventilation is resumed and the laser fiber is withdrawn 5 mm. This cycle is repeated 3-4 times to ensure adequate thermal coverage before switching the fiber to the next access cannula. The procedure is interrupted and ventilation immediately resumed if $SpO_2$ falls below 94% or if the temperature reaches the predefined temperature threshold next to the spinal cord (automatic deactivation).

Immediate Estimation of Thermal Damage

Upon completion of the thermal ablation, the patient is returned to the magnet and T1-weighted (pre and post contrast) sequences of the treated area are obtained with respiratory arrest. The investigators fuse the images and subtract the non-enhancing tissue in order to estimate the area or volume of tumor that has been immediately ablated by the treatment (FIG. 7A). This subtraction image emphasizes the degree of immediate necrosis to estimate the total amount of tumor ablated (FIG. 7B). A 5-mm radius of thermal damage is created per fiber.

Delivery of Spinal Stereotactic Radiation

The pre-operative CT scans and MRI of the spine are used to outline the gross target volume (GTV) and clinical target volumes (CTV). Overall, the fractionation regimen is prescribed based on prior irradiation history, tumor radiosensitivity, tumor volume, and number of vertebral bodies involved. All patients received either a single fraction (24 Gy) or hypofractionation (24 to 27 Gy in 3 doses) and most patients were treated within 3 days of the ablation. The treatment plan was calculated to limit the spinal cord dose to 12 Gy, and to maximally cover the GTV, as if no ablation had been performed.

Evaluation of Degree of Epidural Tumor Compression

The investigators obtained MRI with and without contrast pre-operatively and every 8 weeks after the complete treatment (ablation and SBRT). To quantify the epidural compression, the investigators outlined the contours of the spinal canal and measured the thickness of the epidural tumor on the axial images with the highest degree of spinal canal narrowing. All patients had the degree of epidural compression scored using criteria established by Bilsky et al. (26): Grade 0: tumor completely contained inside the vertebral body; Grade 1a: tumor extending to the epidural space without displacement of the dura; Grade 1b: tumor compressing the dura, without touching the spinal cord; Grade 1C: tumor compressing the dura, touching the spinal cord without displacement; Grade 2: tumor compressing and displacing the spinal cord, but with a column of CSF visible posterior to the cord; and finally Grade 3: epidural compression displacing the spinal cord with complete obliteration of the CSF space. For tumors caudal to the conus medullaris, the investigators adapted the scoring system by adding a virtual spinal cord (with the same area measurement at T10) in the center of the spinal canal. The epidural tumor was classified based on the mass effect in relation to this virtual spinal cord.

Statistical Analysis

Statistical analysis was performed using a Paired Student's t test for the mean thickness of the epidural space and a Wilcoxon signed rank test for the median change in the Bilsky classification, changes in VAS for pain and quality of life. A p value of <0.05 was considered significant.

Results—Study 1

Patient Population

The investigators treated 11 patients (9 males and 2 females) with this technique. The median age was 56 years (range 33-78 years). Six patients had renal cell carcinoma, 2 patients had pheochromocytoma and one case each had melanoma, synovial sarcoma and hepatocellular carcinoma. The thoracic spine was the most commonly mobile spine segment with 7 cases, followed by the lumbar spine with 3 cases and the cervical spine in 1 case (Table 1).

Tumor Location in Relation to the Spinal Cord and Position of the Probe

The location of the tumor influenced the direction of approach for placement of the laser probe. Tumors located in the pedicle and posterolateral vertebral body were more easily accessed than tumors located centrally at the midline. Tumors located in the lamina were accessed through a contralateral translaminar approach. The presence of hardware (titanium or platinum) can influence the quality of the temperature mapping, since the gradient echo sequence used to acquire the thermal imaging is much more sensitive to metal than fast spin echo T1- or T2-weighted sequences. One patient, who presented with a recurrent synovial sarcoma at C2, had undergone two prior attempts for en bloc resection that were supplemented with instrumentation as well as an ipsilateral vertebral artery embolization, leaving titanium screws contralateral to our approach (C1-3) and platinum coils at the level of C1 and C5. In this case, however, the investigators were able to obtain a window without artifact at the exact level of tumor recurrence, which allowed for good thermal mapping. In our experience, tumors in the thoracic spine and thoraco-lumbar junction are easier to access than those in the lower lumbar spine, which usually require an extreme lateral approach to reach the epidural space. In all cases, however, a transpedicular route was used, the lone exception being the aforementioned patient who underwent a C2 ablation, where a direct intratumoral puncture was utilized.

Status of Systemic Disease

Seven patients had progressive systemic disease and were in process of changing chemotherapy regimens due to systemic failure. The most common site of disease progression was the lungs (5 patients), followed by liver (2 patients) and extraspinal bone (2 patient). In all cases, performance of open spinal surgery would have delayed the initiation of systemic treatment.

Three patients were classified as having concurrent diagnosis of the primary tumor (2 renal cell carcinomas and one pheochromocytoma) with spinal and extraspinal metastasis. They all underwent an open abdominal surgery to remove the primary tumor in less than two weeks after the spinal ablation.

Grading Epidural Spinal Cord Compression (ESCC) and Spinal Instability

All patients had epidural tumor compressing the spinal cord or cauda *equina*. Three patients had the dura-mater pushed by tumor touching the spinal cord (ESCC grade 1C). Four patients had tumor displacing the spinal cord with a column of CSF present in the posterior aspect of the spinal cord (ESCC grade 2), whereas 4 patients had no CSF visible around the spinal cord (ESCC grade 3).

The SINS scores were recorded and 3 patients were considered stable (SINS=0-6 points) and 8 patients were scored as potentially unstable (SINS 7-12 pts). One patient was considered at high risk of instability (SINS=12) and had percutaneous placement of pedicle screws performed at the time of laser ablation. One patient had an en bloc resection and cervical spinal stabilization performed in a prior operation outside our institution and was considered stable by virtue of the prior instrumentation. Finally, one patient developed significant mechanical pain 2 months after the ablation and had placement of percutaneous pedicle screws supplemented with vertebroplasty.

Duration of the Procedures

All patients were admitted on the same day of the procedure. The average length of the ablations was 8 hours. This time included patient anesthesia and positioning, obtaining the fluoroscopic match for navigation, placing the access cannulas into the desired location in the epidural tumor, transferring the patient into the MRI magnet, obtaining the localization for each fiber, obtaining the parameters for the thermal map for each fiber, performing an average of 5 cycles of heating per puncture with ventilator pauses, evaluation of SSEP monitoring between each cycle, obtaining a final scan with and without contrast for evaluation of the ablated tissue, closing the stab wounds, and transferring the patient to a stretcher for extubation. All patients recovered well, without deficits or complaints. Pain was minimal and all patients had a short hospital stay, unless they had been admitted for concurrent resection of their primary tumor (nephrectomy in patient 6 and adrenelectomy in patient 11).

Estimated Immediate Tumor Ablation

Figure 7:
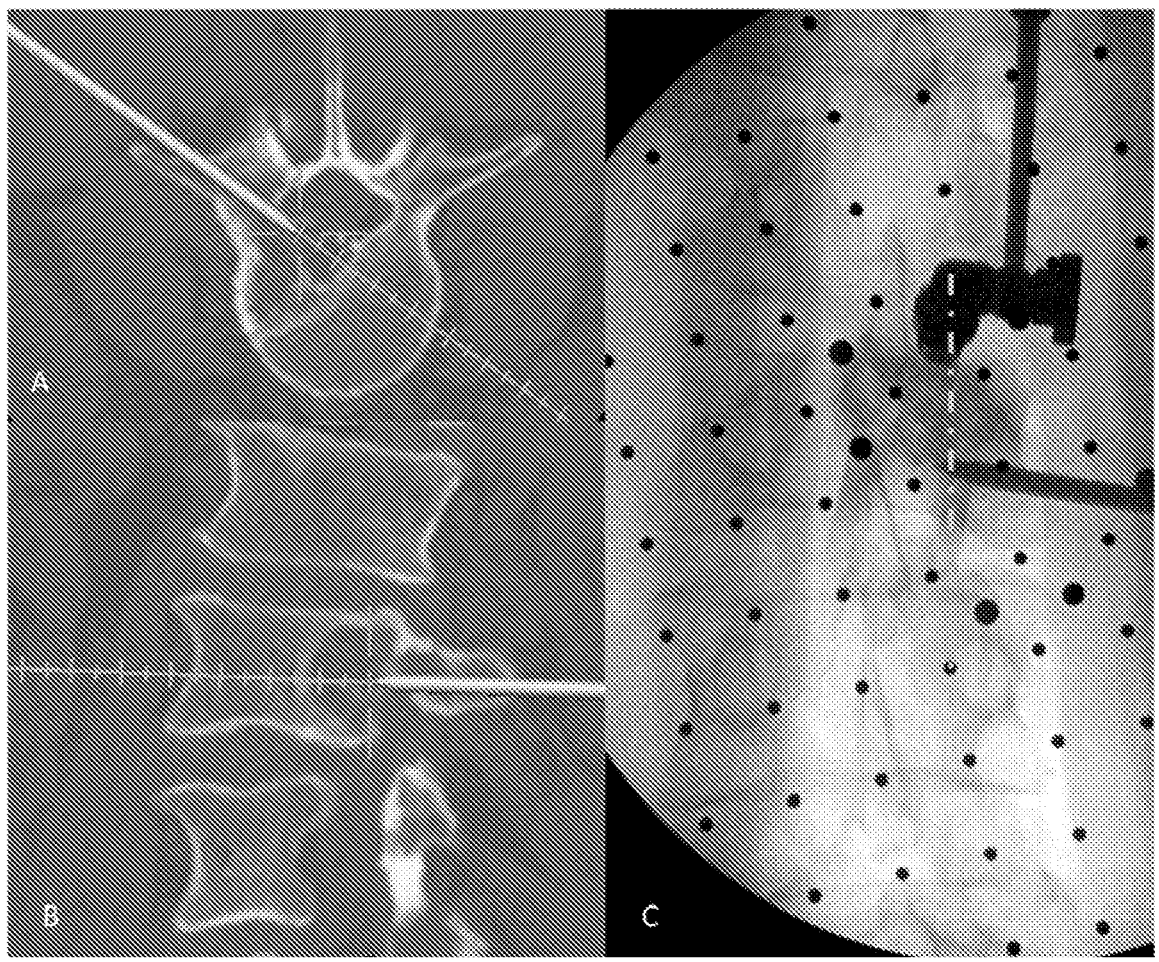
FIG. 7 displays an image guidance technique for percutaneous placement of the laser probe according to the present disclosure.

The ablated tumor can be estimated by the final post-contrast subtraction axial images (FIG. 7). The area of non-enhancement on this image corresponds to tumor that was immediately destroyed by the ablation. Based on our observations, the investigators estimate that each treatment immediately destroys on average 36.2% of the tumor, where each fiber provides a 10 mm diameter lesion and the total area of damage is proportional to the number of fibers. (Table 2)

Morbidity and Hospital Stay

All patients were admitted to regular hospital beds after the procedure and the median hospital stay was 2 days. No patient had decline in performance status or major neurological dysfunction. The patient with cervical synovial sarcoma (patient 5), who had direct placement of the laser probe into the tumor, reported experienced tingling in the entire lower extremity and posterior aspect of the right arm, sparing the hands and feet with decreased perception of temperature that started 72 hours after the procedure. On exam, this patient was otherwise neurologically intact, displaying no changes of motor coordination, proprioception, gait, muscle strength, reflexes, or pain perception. Given this complaint, the investigators obtained an MRI of the cervical spine which demonstrated near complete ablation of the tumor, without progression of epidural disease or increase in the spinal cord compression, however, a faint T2 hyperintensity in the left lateral aspect of the spinal cord at the level of C2 not present on the immediate post-ablation scan was observed. The investigators believe this cord signal change represented a delayed effect of the thermal ablation, which caused mild edema in the spinal cord and a partial dysfunction of the lateral spinothalamic tract with sparing of the anterior spinothalamic tract. The investigators delayed the SSRS for 4 weeks until the investigators confirmed complete resolution the T2 abnormality with a new MRI. Patient's symptoms subsided on 4-week follow up.

One patient with renal cell carcinoma (patient 6) previously treated with bevacizumab, presented with post-operative dehiscence and infection of the midline incision performed to anchor the spinous process clamp used for image guidance. This patient underwent debridement, received intravenous antibiotics and placement of a wound vacuum and healing is ongoing by secondary intention.

Post-Procedure Image Control and Treatment Failures

Image follow up with MRI was performed 8 weeks after procedure in all patients. The investigators noted that all individuals developed an area of central coagulative necrosis, with peripheral contrast enhancement outlining the treated region. The investigators measured the thickness of the epidural tumor at the level of maximal epidural compression before and after treatment in all patients (Table 3). The investigators noted a mean reduction of 27.8% in the median thickness of the epidural tumor on the 8-week follow-up imaging. The mean thickness of the epidural tumor decreased significantly from 8.82 mm (95% CI 7.38-10.25) prior to treatment to 6.36 mm (95% CI 4.65-8.07) on the 2-month follow-up MRI, (p=0.0001). Our current median follow up is 4.7 months (range 3.4-6.6 months), and no change on the thickness of this epidural enhancement was noted on the patients with image follow up available beyond 8 weeks from the procedure.

In order to quantify the improvement based on the ESCC score, the investigators converted each category to a number. The median pre-operative score was 4 (range 3-5), which was significantly higher than the median of the 2-month post treatment score of 2 (range 1-5), (p=0.04, Wilcoxon test).

One patient with renal cell carcinoma metastatic to L3 (Patient 8) had a myelographic blockage (Grade 3 ESCC) prior to treatment. This individual developed intractable radicular pain despite a modest reduction in the thickness of the epidural tumor at image follow up at 4 weeks after ablation and SBRT. He underwent a posterior transpedicular vertebrectomy with polymethylmethacrylate reconstruction of the vertebral body and pedicle screw stabilization with significant improvement of his pain and performance status. Another patient with hepatocellular carcinoma had the epidural tumor unchanged (stable), and continues to have improvement in pain and quality of life. All other patients (9 out of 11), had favorable response, with decrease in at least one degree in the ESCC.

Pain and Quality of Life Measures

Figure 8:
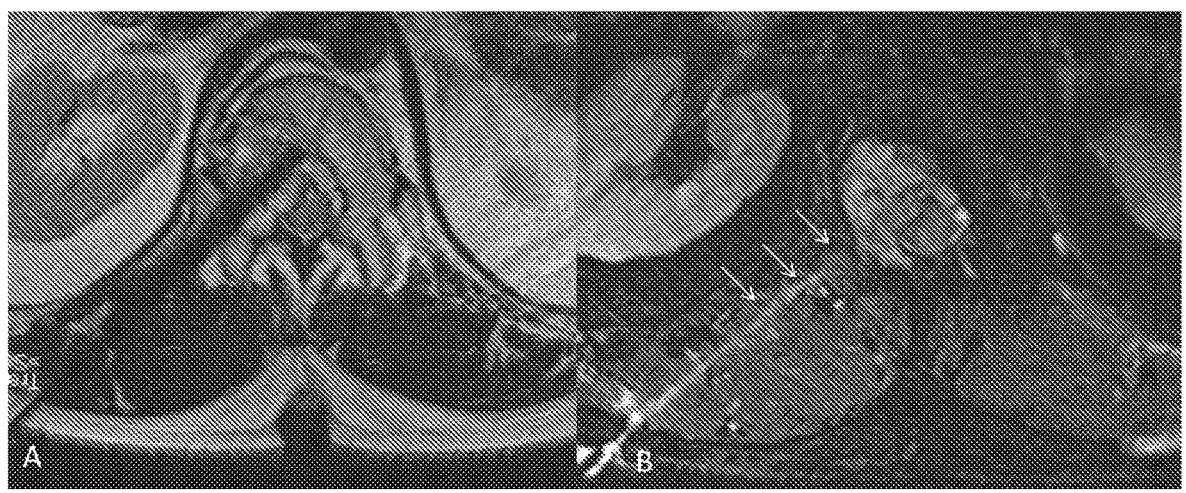
FIG. 8 displays an intraoperative localization of the laser fiber according to the present disclosure.

The mean pre-operative VAS for pain was 6.18 (SD=2.27), which was significantly higher than the score of 4.27 (SD 2.32) p=0.035, observed within 30 days or 2.8 (SD 1.88) p=0.01, obtained within 60 days. The median VAS for quality of life remained stable without significant changes rated 60%; 70%; 70% respectively at pre-op, within 30 days (p=0.09) and within 60 days after treatment (p=0.31) (FIG. 8). One patient underwent a nephrectomy and one had an adrenalectomy less than 2 weeks after our procedure, and the investigators believe the pain scores and quality of life were negatively influenced by these procedures.

Discussion

The investigators report for the first time the use of laser interstitial thermotherapy in the treatment of tumor located in the epidural space of the spinal canal. The investigators had to overcome a series of challenges to utilize this technology in the spine. Percutaneous techniques are commonly used to perform minimally invasive spinal procedures, but all image guidance modalities and instruments are based on CT scans, therefore there is no current image guidance method that allows obtaining an MRI scan to acquire the parameters for navigation. The investigators utilized a high resolution CT scan and fused with AP and lateral fluoroscopic images, allowing the use of CT images to identify the contour of the spinal canal The length of the procedure is dependent on a learning curve. Optimization of the imaging guidance for placement of the probe and the localization studies to identify the correct plane of the probe can significantly shorten the operative time. One useful strategy is placement of a titanium needle inside each access cannula, which creates an artifact that aids in localizing correct anatomic plane of the laser fiber to perform the thermal images. In order to obtain a reliable thermal mapping it is imperative that respiratory motion is interrupted, the investigators limit the time for each cycle of breath holding for no more than 2 minutes. If needed, additional cycles can be performed until a satisfactory coverage of the tumor is achieved.

In general, heat delivered by the laser requires water to dissipate [39]; therefore, there are differences in the size of the tumor covered by a single fiber in different organs. In general, bone is an unfavorable tissue for large coverage with this method. Our results estimate that each fiber can cover approximately an 8-10 mm radius, assuming that heat will spread in an oval shape around the fiber. Unlike in the brain, there is virtually no morbidity to taking multiple trajectories in order to achieve coverage of the epidural tumor. The investigators have used up to 6 punctures and bilateral transpedicular approaches without any complication. Even highly vascular tumors tolerate multiple punctures well, and no significant bleeding was encountered. If bleeding occurs, the investigators place hemostatic foam and insert the titanium needle inside the access cannula for a few minutes to tamponade the bleeding source.

Another interesting observation is the fact that the spinal cord is located in a completely different compartment than the epidural tumor. The investigators observed no swelling of ablated tumor into the spinal canal, likely because these tumors are contained by the posterior longitudinal ligament (PLL), epidural veins and periosteum, a distinction from the ablation effect in intrinsic brain tumors, where steroids are recommended to decrease tumor swelling. Also, the CSF serves as a heat sink and in the levels where it was present, the investigators could see on thermal imaging the heat contouring the spinal canal and dissipating in the CSF. The system has capability of monitoring up to 3 safety points and once the temperature reaches the predefined limit of 50° C., the system automatically shuts off. The investigators theorize that heat spreads as an ellipse or a circle and therefore its most medial extent is at the level of the axial plane of the fiber in relation to the spinal cord. The investigators monitor our safety points along the exact axial plane of the fiber, because failure to do so could result in severe neurological damage. One of our patients (patient 5) had no CSF interposed between the C2 tumor and the spinal cord and her tumor was exclusively in the epidural space; therefore, there was no pseudocapsule of PLL, periosteum and epidural veins. In this case, the investigators set the laser to stop immediately at the interface between tumor and the spinal cord. Unfortunately she developed T2 signal changes in the spinal cord, which were associated with tingling in the lower extremity compatible with a partial spinothalamic dysfunction. The investigators believe that a more conservative approach is needed in such cases, utilizing lower temperatures and placing the voxel monitoring the temperature inside the tumor and not in the interface between the tumor and the spinal cord.

The great majority of our patients had symptomatic improvement of pain shortly after the procedure. The investigators have obtained VAS for pain and quality of life in all patients within 30 and 60 days, with most patients reporting a brief pain flare around 3-7 days after the SBRT. Overall, subjective patient satisfaction was very high and the hospital stay was shorter than conventional surgery. The only exception was the patient who did not respond to treatment and developed intractable radicular pain (Patient 8). In this case, the investigators performed the standard surgical treatment for which he would have been considered, without adverse events or significant additional delay in initiation of chemotherapy.

All patients developed a ring enhancing pattern in the post-procedure spinal MRI (FIG. 7). The nature of this contrast enhancement in the epidural space is uncertain, and could represent engorgement of the epidural veins, inflammation related to heat damage, development of scar in the posterior longitudinal ligament, residual viable tumor, or a combination of those. The investigators have had 4 patients with 6 months of imaging follow up and no change on the thickness of this epidural enhancement was noted.

This report represents our initial experience with the technique and the investigators recognize several limitations, including: small size of the cohort, short follow up, lack of randomization, no direct comparison with surgery, and no standardization in the time for post-procedure SSRS. The investigators believe this report lays the foundation for further investigation, with a randomized prospective study to compare this technique to separation surgery prior to SSRS.

In conclusion, the investigators present a minimally invasive technique associated with minimal blood loss, minimal hospital stay, and minimal impact in quality of life, minimal surgical morbidity which is associated with improvement of pain and most importantly, avoids interfering with initiation of treatment for systemic disease. The investigators believe this procedure can be an alternative to separation surgery in patients without neurological deficits prior to SSRS, especially in patients with progressive systemic disease, where conventional surgery would be of high risk for complications and associated with interruption or delays in the delivery of the intended oncologic treatment.

FIG. 7 displays an image guidance technique for percutaneous placement of the laser probe. FIG. 7A shows axial and FIG. 7B shows sagittal CT reconstruction used for navigation of the Jamshidi needle. Accuracy in the sagittal plane is confirmed when the tactile sensation of the needle touching bone corresponds to perfect contact of the virtual needle with the cortical surface of the lamina. The needle is deepened until the lateral and medial wall of the pedicle is reached. FIG. 7C shows a fluoroscopic image in anteroposterior projection is taken during needle advancement and compared to the navigation image for assurance of accuracy. The investigators use the medial wall of the pedicle inferior to the tumor to draw a reference line (dotted line) for the level of interest. In this example, the navigation image is compatible with the current location of the needle in the inferior portion of the pedicle just passing the medial wall into the vertebral body.

FIG. 8 displays an intraoperative localization of the laser fiber. FIG. 8A shows an axial image demonstrating the titanium needle artifact in the epidural tumor. The coordinates are stored and the titanium insert is removed and replaced by the laser fiber. FIG. 8B shows an axial T1-weighted image with fat suppression, used to localize the laser fiber (arrows) based on the coordinates obtained from the same location of the image in FIG. 8A.

Figure 9:
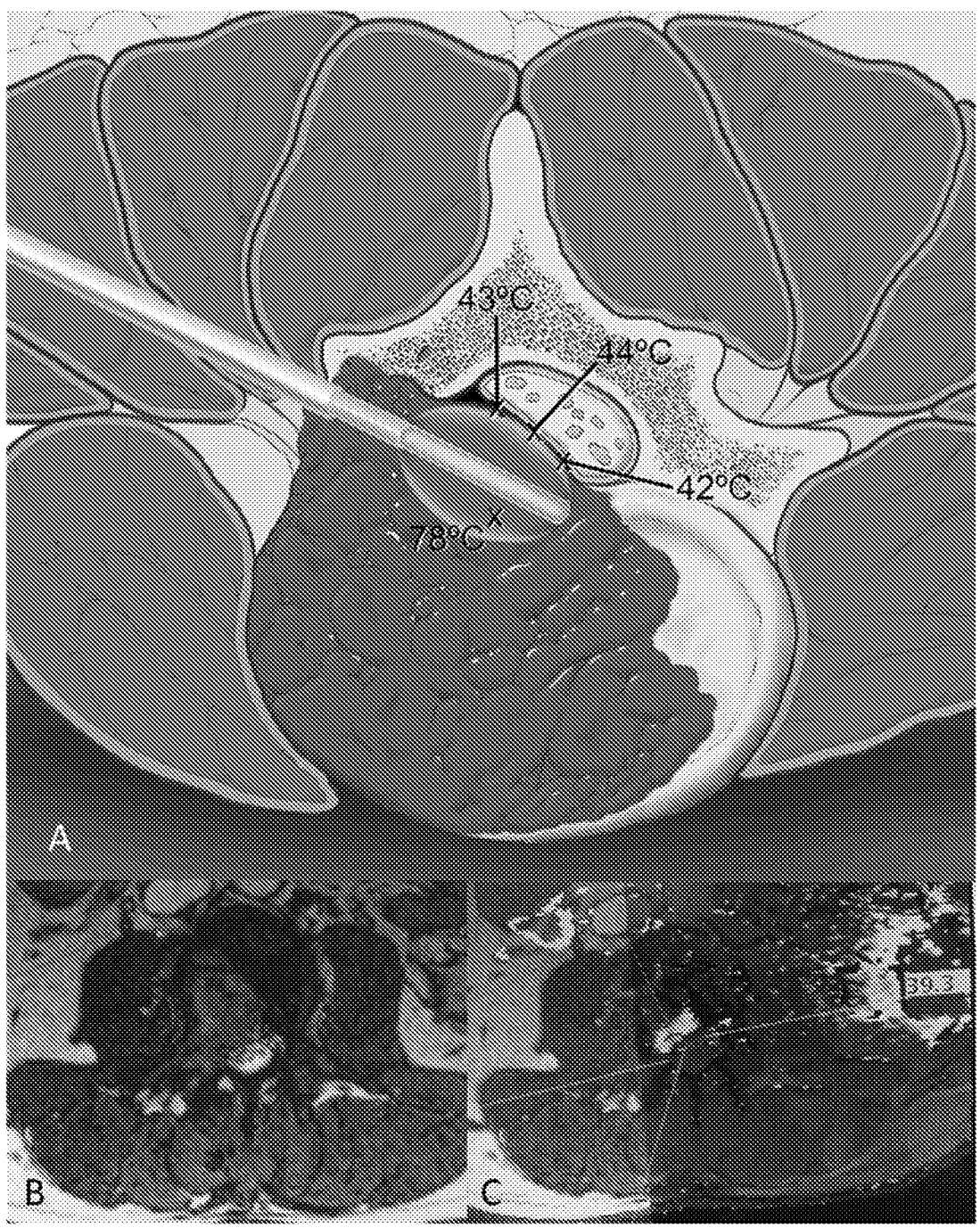
FIG. 9 shows an intra-operative temperature monitoring according to the present disclosure.

FIG. 9 shows an intra-operative temperature monitoring. FIG. 9A shows an artist illustration demonstrating the final placement of the laser probe in the epidural tumor. The investigators monitor the temperature in 3 points at the junction of the tumor and the dura, with a safety limit of 50° C. The temperature near the laser fiber is monitored and a limit of 90° C. is set to avoid vaporization of the tissue, which prevents adequate spread of the heat. FIG. 9B shows an axial T2-weighted image used to select the points near the dura which will be monitored in order to protect the neural elements. FIG. 9C shows intraoperative footage of the thermal map overlaid to the corresponding anatomic T2 image demonstrating the real time monitoring of the spread of heat and temperature at the selected points in the epidural space.

Figure 10:
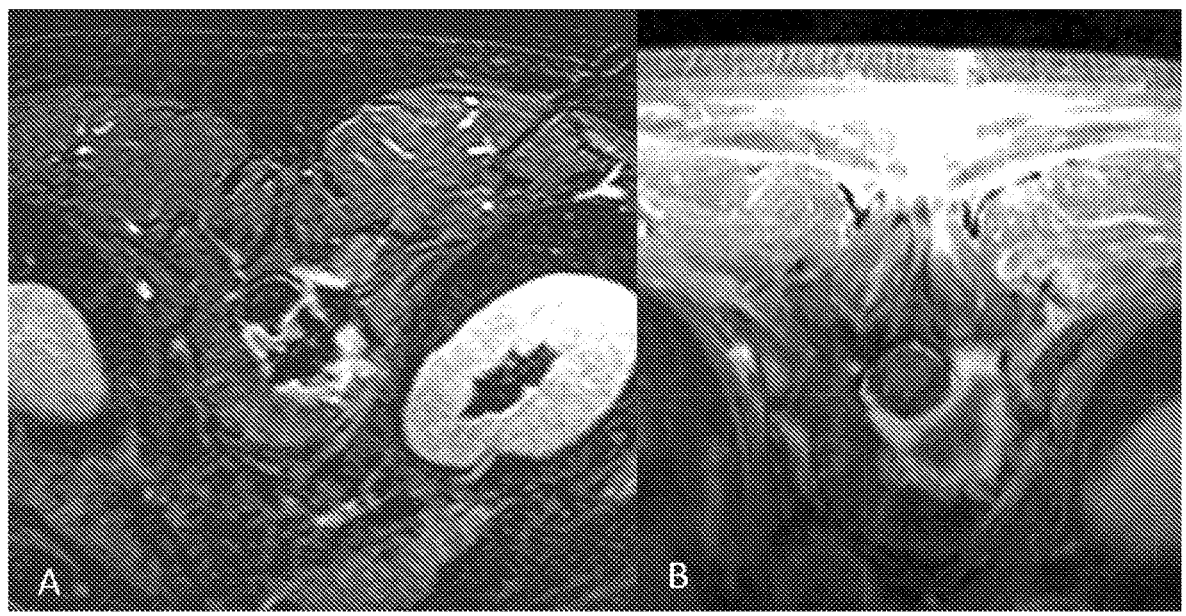
FIG. 10 shows an estimation of the thermal damage and correlation with standard image follow up according to the present disclosure.

FIG. 10 shows an estimation of the immediate thermal damage and correlation with standard image follow up. FIG. 10A shows immediate axial T1-weighted post contrast subtraction image (pre-contrast image subtracted from the post-contrast image). Subtraction emphasizes the enhancing areas and shows immediate post-procedure coagulative necrosis to better advantage. Note that there is mild ventral epidural mass effect. FIG. 10B shows axial T1-weighted image with contrast at the same level of image of FIG. 10A, obtained 2 months after the ablation demonstrating resolution of the epidural mass effect.

Figure 11:
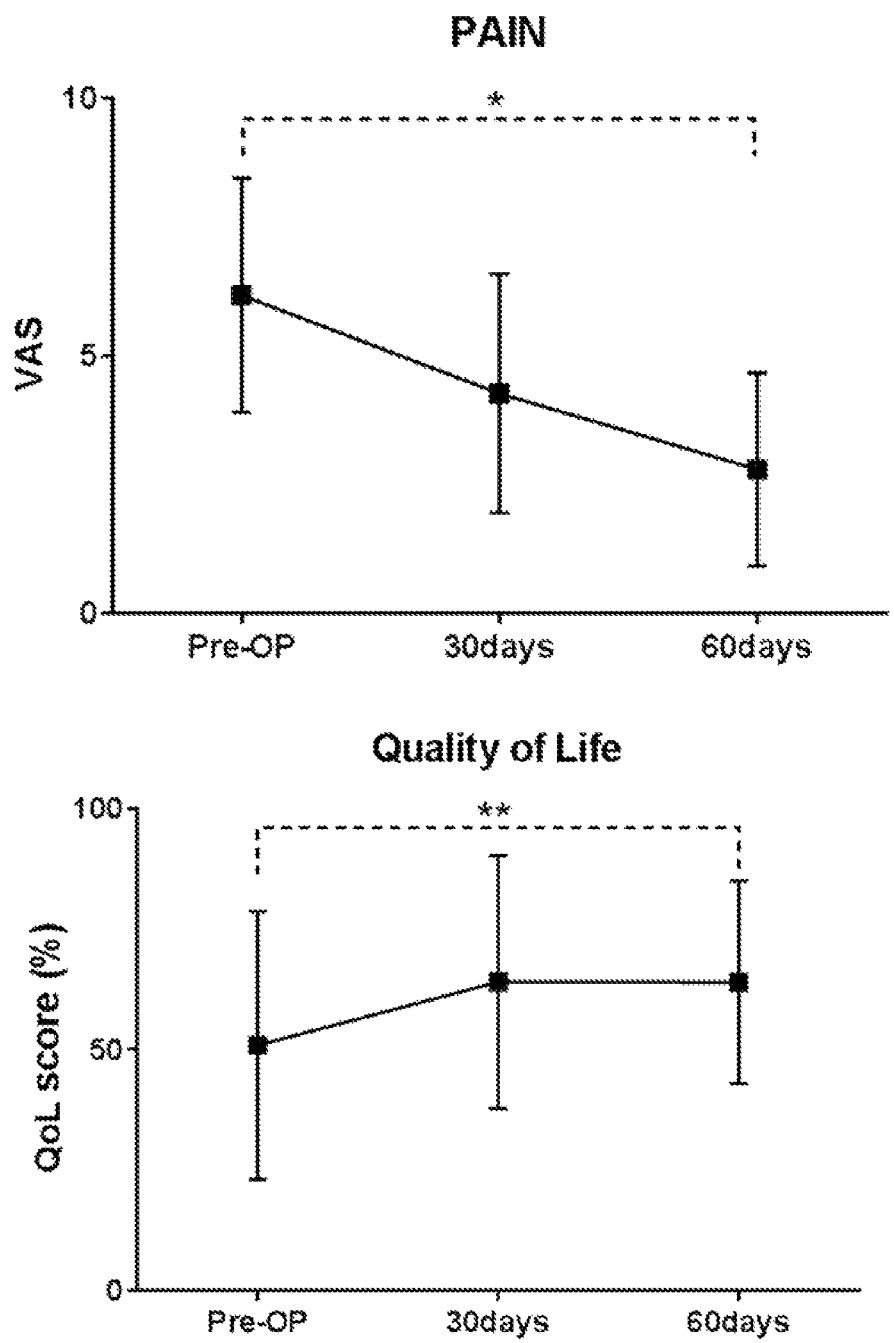
FIG. 11 shows a visual analog scale of pain and quality of life for patients having undergone procedures according to the present disclosure.

FIG. 11 shows a visual analog scale of pain and quality of life. FIG. 11A displays a graph demonstrating the VAS score for pain over time. FIG. 11B shows a graph demonstrating the VAS score for quality of life over time. * $p<0.05$, ** $p>0.05$, statistical significance was determined using Wilcoxon Signed Ranks test.

TABLE 1

Patient Demographics Enrolled in Study

| Case | Age/sex | Primary tumor | Level | Pre-OP KPS (%) | SINS score | Hospital stay (days) | Time from OP to SSRS (days) | SSRS dose (Gy/Fr) | remark |
|---|---|---|---|---|---|---|---|---|---|
| 1 | 54/F | RCC | L3 | 60 | 8 | 1 | 1 | 24/3 | |
| 2 | 71/M | Melanoma | T2 | 50 | 10 | 1 | 26 | 24/3 | prior cEBRT |
| 3 | 64/M | RCC | T10 | 90 | 7 | 2 | 4 | 24/1 | |
| 4 | 78/M | RCC | T12-L1 | 90 | 8 | 2 | 3 | 27/3 | |
| 5 | 33/F | Synovial SA | C2 | 90 | n/a | 1 | 45 | 24/3 | Prior fusion and cEBRT |
| 6 | 46/M | RCC | T12 | 60 | 12 | 16 | 3 | 24/1 | followed nephrectomy |
| 7 | 57/M | RCC | T4 | 90 | 5 | 4 | 3 | 24/1 | |
| 8 | 56/M | RCC | L4 | 50 | 9 | 7 | 3 | 24/1 | |
| 9 | 58/M | Pheocromo | L3 | 90 | 5 | 1 | 3 | 24/1 | |
| 10 | 52/M | HepatoCA | T12 | 60 | 10 | 3 | 2 | 24/1 | |
| 11 | 39/M | Pheocromo | T11/T12 | 80 | 7 | 8 | 60 | 27/3 | followed adrenalectomy, Prior cEBRT |

RCC, renal cell carcinoma;
HCC, Synovial SA, synovial sarcoma;
HepatoCA, Hepatocarcinoma;
Pheochromo, pheochromocytoma;
OP, operation;
ESCC, epidural spinal cord compression;
n/a, not available,
KPS, karnofsky performance scale;
SINS, spine instability neoplastic score

TABLE 2

Detail of treatment parameters in 11 patients performed laser interstitial thermotherapy

| case | Estimated tumor area (cm$^2$) | Estimated ablated area (cm$^2$) | Percentage of tumor ablated (%) | Number of fibers | Average distance from the fibers to dura (mm) |
|---|---|---|---|---|---|
| 1 | 27.48 | 8.02 | 29.1 | 2 | 9.5 |
| 2 | 5.1 | 1.00 | 19.6 | 2 | 5.8 |
| 3 | 6.94 | 1.57 | 22.6 | 3 | 5.2 |
| 4 | 13.95 | 2.85 | 20.4 | 4 | 5.8 |
| 5 | 1.61 | 1.12 | 69.6 | 3 | 5.1 |
| 6 | n/a | n/a | n/a | 4 | 8.2 |
| 7 | 8.67 | 1.93 | 22.3 | 3 | 5.0 |
| 8 | 8.21 | 2.06 | 23.5 | 2 | 13.7 |
| 9 | 6.29 | 2.28 | 36.2 | 2 | 5.7 |

TABLE 2-continued

Detail of treatment parameters in 11 patients performed laser interstitial thermotherapy

| case | Estimated tumor area (cm$^2$) | Estimated ablated area (cm$^2$) | Percentage of tumor ablated (%) | Number of fibers | Average distance from the fibers to dura (mm) |
|---|---|---|---|---|---|
| 10 | 10.03 | 6.97 | 69.4 | 2 | 8.8 |
| 11 | 4.89 | 2.55 | 52.1 | 2 | 4.7 |
| median | 8.21 | 2.28 | 36.2 | 2 | 5.7 | n/a, not available

TABLE 3

Follow up Clinical and Radiographic Parameters in 11 Patients After Procedure

| | Epidural spinal cord compression | | Greatest Epidural tumor thickness (mm) | |
|---|---|---|---|---|
| Case | Pre-op | 2 months | Pre-op | 2 months |
| 1 | 2 | 1B | 9 | 5 |
| 2 | 3 | 3 | 9 | 6 |
| 3 | 1C | 1A | 6 | 2 |
| 4 | 1C | 1B | 8 | 7 |
| 5 | 2 | 1C | 11 | 8 |
| 6 | 2 | 1B | 8 | 4 |
| 7 | 3 | 3 | 8 | 6 |
| 8 | 3 | 3 | 14 | 12 |
| 9 | 1C | 1B | 7 | 6 |
| 10 | 2 | 3 | 8 | 8 |
| 11 | 3 | 1B | 9 | 6 |
| median | 2 | 1B | 8 | 6 |

Introduction

Image guidance for spinal procedures is typically based on 3D fluoroscopy or computed tomography which provide poor visualization of soft tissues including the spinal cord. To overcome this limitation, we developed a method to register intraoperative MRI of the spine into a neuronavigation system allowing excellent visualization of the spinal cord.

In this study, patients were positioned prone on the MRI table under general anesthesia. Fiducial markers were applied on the skin of the back and a plastic cradle was used to support the MRI coil to avoid skin contact. T2 MRI sequences of the region of interest were exported to a standard navigation system. A reference array was sutured to skin and surface matching of the fiducial markers was performed. A navigated Jamishidi needle was advanced into a target in the epidural space and a screenshot of its final position was saved before exchanging to an MRI-compatible plastic access cannula. MRI of the exact axial plane of each access cannula was obtained and compared to the corresponding screenshot saved during its positioning. The discrepancy in millimeters between the trajectories was measured to evaluate accuracy of the image guidance.

Thirteen individuals underwent implantation of 49 laser probes. The median discrepancy between the location predicted by the navigation system and the actual position of the access cannulas was 0.7 mm (range 0 to 2.7 mm). No injury or adverse event occurred during the procedures.

The feasibility of image guidance is demonstrated based on MRI to perform laser interstitial thermotherapy of spinal metastasis. This method allows excellent visualization of the spinal cord, improving the safety and the workflow during laser ablations in the epidural space. The results can be extrapolated to other indications including biopsies or drainage of fluid collections near the spinal cord.

The incorporation of image guidance technology facilitated the development of new techniques in the care of patients suffering from spinal metastasis. Image guidance was initially used to perform biopsies [41] and was quickly adapted for placement of implants [42] and to aid complex surgical resections [43]. Its incorporation into radiation delivery methods resulted in a new field within radiation oncology labeled as stereotactic body radiotherapy (SBRT) [44]. Over the last decade, development of new platforms such as 3D fluoroscopy, cone beam CT and intraoperative CT have provided surgeons several advantages including improvements in tissue visualization, accuracy of instrument navigation and decrease of exposure of ionizing radiation to operating room personnel and to patients [45-47].

Intraoperative MRI (iMRI) has been commonly used in neurosurgery as valuable tool for cranial procedures ranging from biopsies [48], tumor resections [49], implantation of beep brain stimulators [10] and more recently to perform laser ablation of epileptogenic foci [11] and tumors [37, 51, 52] However, the utilization of intraoperative MRI to perform spinal procedures has been very limited, with just a few reports evaluating its feasibility in surgical decompressions [53] and fenestration of intradural cysts [54-55].

Here, we describe the use of image guidance for spinal laser interstitial thermotherapy (sLITT) [56-57]. This is the first report of utilization of iMRI to provide image guidance for placement of a laser probes in the epidural space for treatment of spinal metastasis. Our results show that implementation of minor modifications in hardware allows this technique to be used in any iMRI, expanding the applicability of laser ablations and MRI guided biopsies in soft tissue.

Methods

Patient Population and Evaluation

This single institution retrospective analysis was reviewed and approved by the MD Anderson Cancer Center institutional review board. All patients had documented spinal metastasis from histologies considered to have unfavorable response to cEBRT. The epidural extension of the tumor was scored based on pre-operative MRI on axial T2 or post-contrast sequences according to the method described by Bilsky et al [26]. Spinal stability was assessed by using the spine instability neoplastic scale (SINS score) as described by Fisher et al. [58]. All cases were presented in a multidisciplinary tumor board conference with neurosurgery, radiation oncology and radiology, during which consensus was reached that separation of the tumor was needed prior to SSRS. The utilization of the hardware and software in this report using MR images for spinal navigation is investigational and corresponds to an off label use of such technology. Operative data included the intraoperative MR and fluoroscopic images and the screen shots from the navigation system screen. All images used for analysis were de-identified. The study radiologist (B.A.) performed the measurements between the closest point of the dura in relation to the predicted and final trajectory of fiber implantation as described below.

Image Guidance Technique for Placement of the Laser Probe in the Epidural Space

Figure 12:
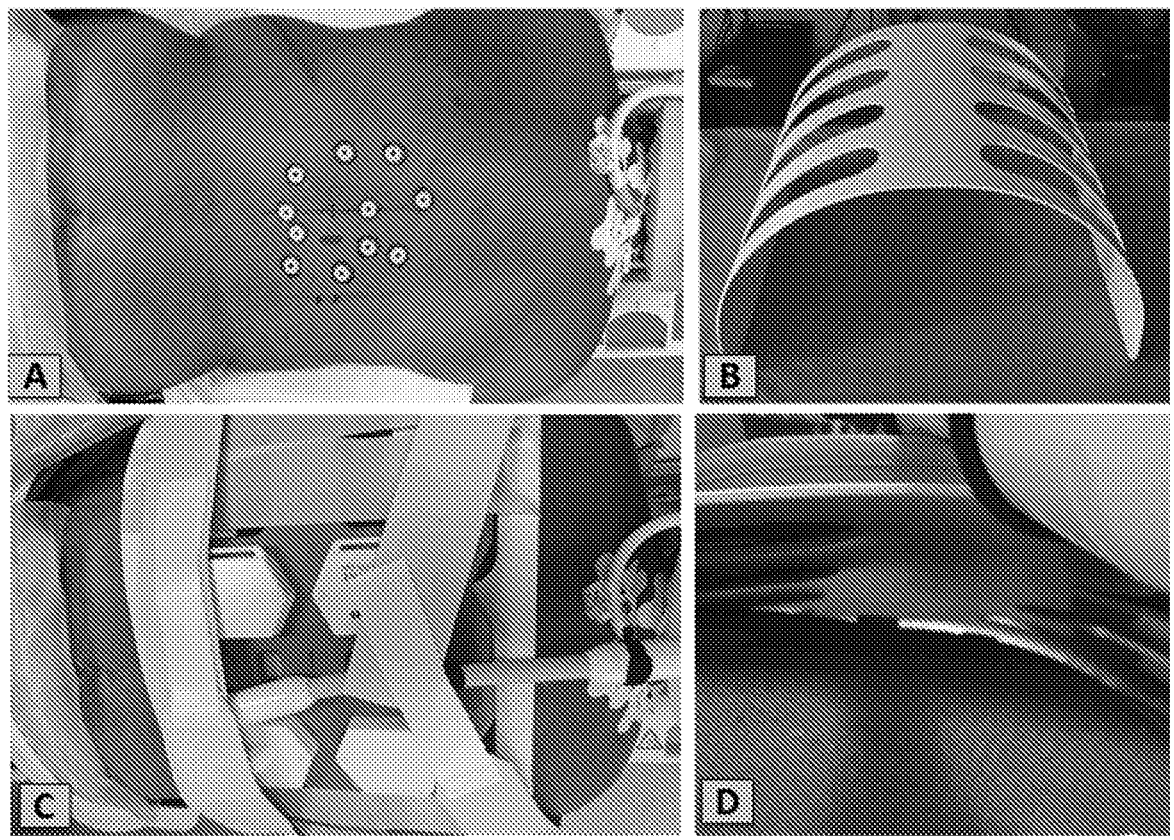
FIG. 12 shows photographs of a patient during various steps of an exemplary method according to the present disclosure.
Figure 13:
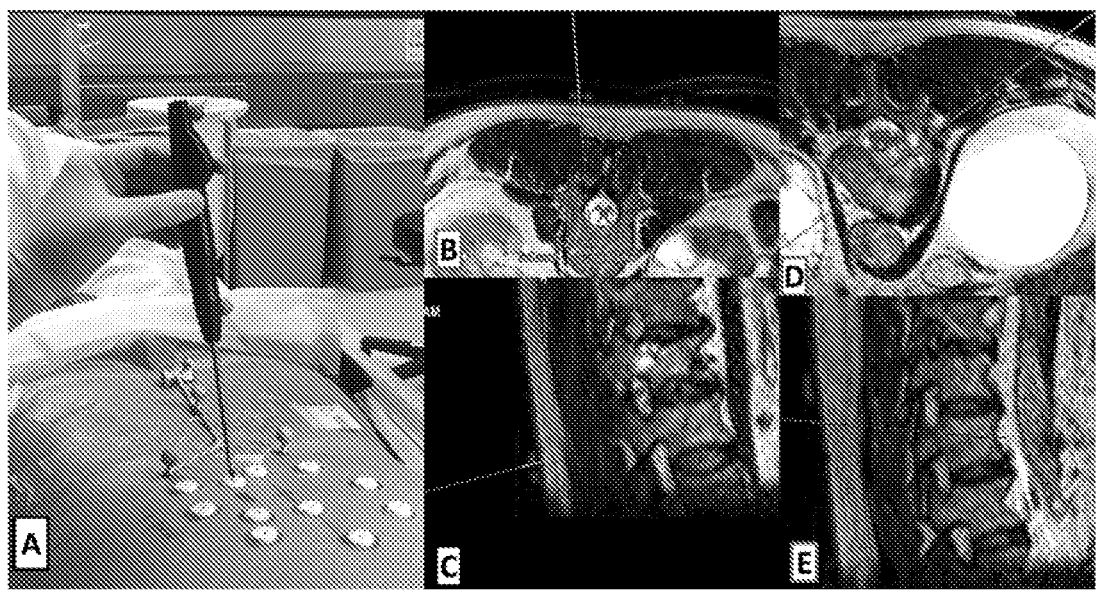
FIG. 13 shows photographs and MRI images of the patient during subsequent steps of the method of FIG. 12.
Figure 14:
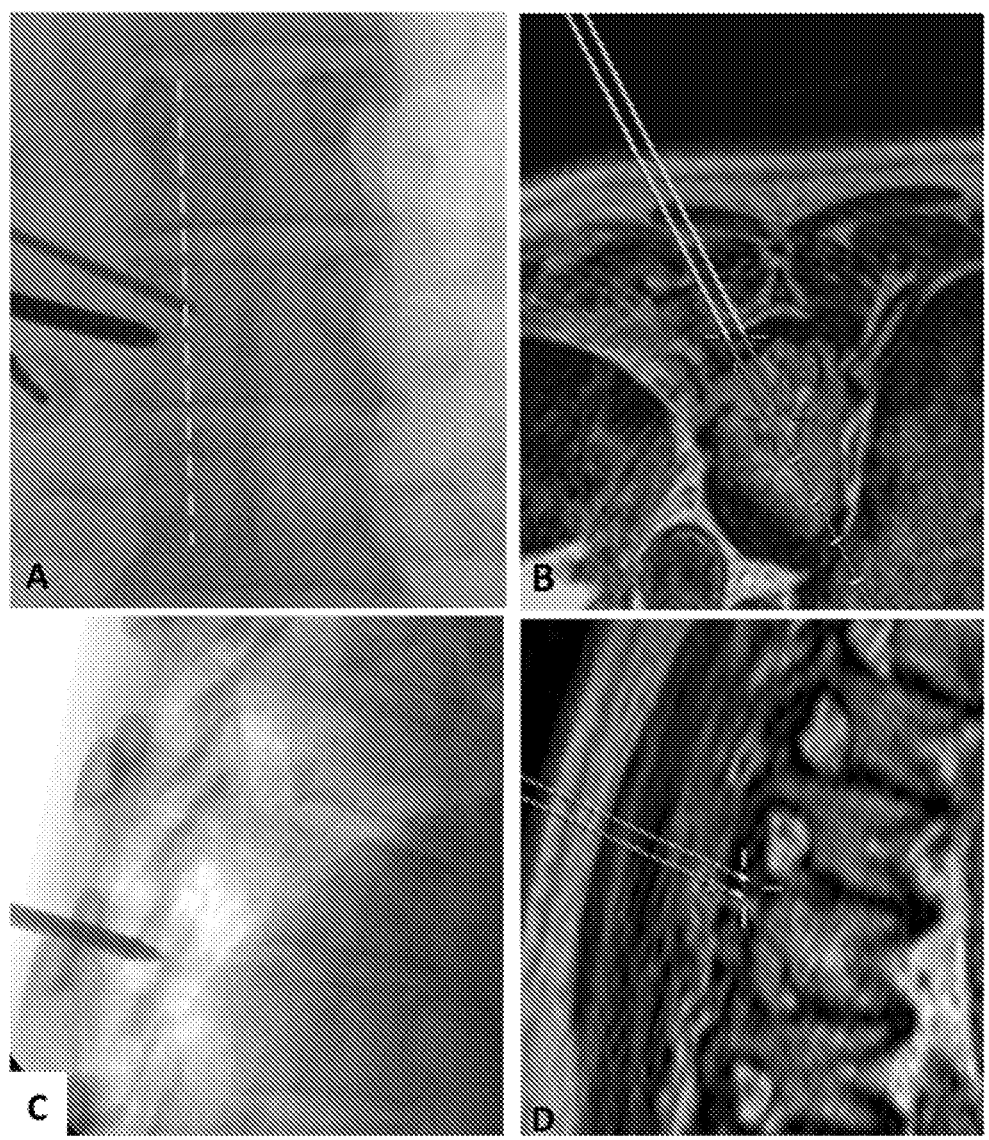
FIG. 14 shows anterior-posterior (AP) MRI images of the patient during subsequent steps of the method of FIG. 12.
Figure 15:
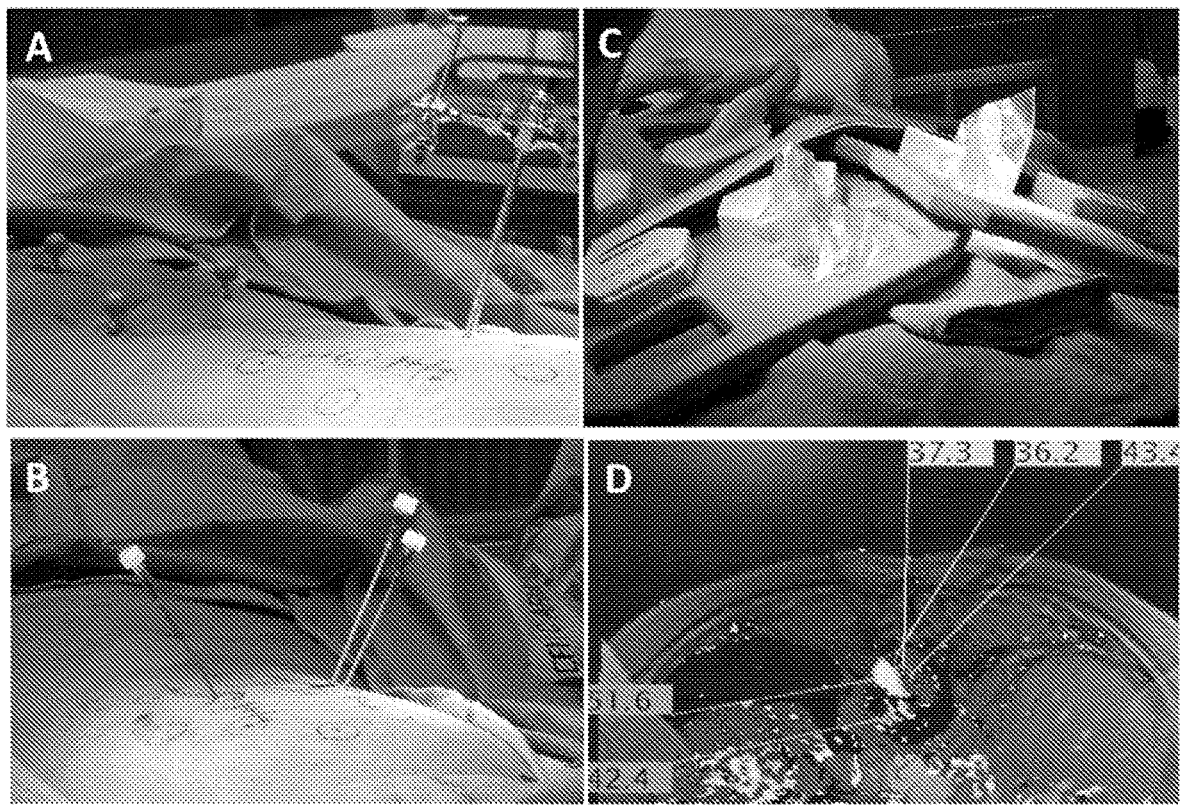
FIG. 15 shows photographs and MRI images of the patient during subsequent steps of the method of FIG. 12.

The procedure is performed inside the iMRI (BrainLab Inc, Feldkirchen, Germany). After general endotracheal anesthesia is induced, the patient is positioned prone over gel rolls placed in parallel along the patient body axis with the arms tucked to the side over the iMRI transfer table. A fluoroscope (Siemens, Germany) is positioned inside the room at a safe distance from the MRI to give obtain anteroposterior and lateral fluoroscopic images. The level to be treated is localized and standard fiducial markers (Izi medical products, Owings Mills, Md.) are placed on the skin overlying the operative level (panel A of FIG. 12), a Siemens body matrix coil is taped over a plastic cradle (panel B of FIG. 12) and placed over the patient taking care to not touch the underlying skin and fiducials (panels C and D of FIG. 12). The patient is transferred to the MRI machine and a T2 sequence of the region of interest is obtained. The images are transferred to the workstation of the image guidance system (Brainlab, Inc.) where a 3D model of the spinal segment containing the fiducials is created. A reference point is added in the center of each fiducial marker in contact with the patient's skin and this plan is exported to the navigation system. The patient is removed from the MRI magnet and the transfer table repositioned in front of the c-arm. The skin adjacent to the fiducials is prepped and a reference array is secured with stitches and adhesive drape. A surface match of the fiducials is performed taking care to avoid displacement of the skin. Accuracy of the navigation is easily verified by placing the navigation probe inside the fiducials (panels A, B and C of FIG. 13) and at the midline overlying an easily palpable spinous process. Once this initial verification is considered accurate by the surgeon, an offset of 70 mm is added and image guidance in the inline axial and the sagittal projections are used to identify the proper trajectory in order to reach the epidural tumor at an approximate distance of 5 to 6 mm from the edge of the dura mater (panels D and E of FIG. 13). A navigated Jamshidi needle (DePuy, Synthes) registered to the navigation system is advanced through the soft tissues until it reaches the lamina of the vertebral body affected by tumor. If the lateral projection of the navigation image is compatible with the tactile sensation of touching bone, the needle is docked in the lamina. At this stage, an AP fluoroscopic image is obtained (FIG. 14), and the surgeon compares the predicted location of the needle with the current AP projection using the pedicle of the adjacent level as a reference for the limits of the spinal canal. If accuracy is satisfactory; the needle is advanced towards the pre-defined target and a snapshot of its final position is saved. At this stage, the central trocar is removed, and a K-wire is placed through the Jamshidi needle, which is subsequently removed. The K-wire is used as a guide for placement of a non-ferromagnetic plastic access cannula. It has been our experience that a distance of 5-6 mm around each side of the laser fiber will generate temperatures high enough to induce tumor cell death. If more coverage is needed, additional access cannulas are placed in tandem at a 10-12 mm distance in order to cover the cranio-caudal extension of the epidural tumor. Lastly, an MRI-compatible titanium needle is inserted into the access cannula and docked into the residual bone of the vertebral body and a sterile plastic bag is used to cover the needles (FIG. 15).

In order to obtain good quality of images for the MRI thermography, we use two standard Siemens body matrix MRI coils placed on each side of the patient's back, overlapping in the center and held by straps. The patient is placed into the MRI magnet and T2 HASTE sequence is used to localize the artifact of the titanium needles, which allows final confirmation of their trajectory. The ablation of the epidural tumor is performed as previously described. [56].

Final Accuracy of the Needle Positioning

Figure 16:
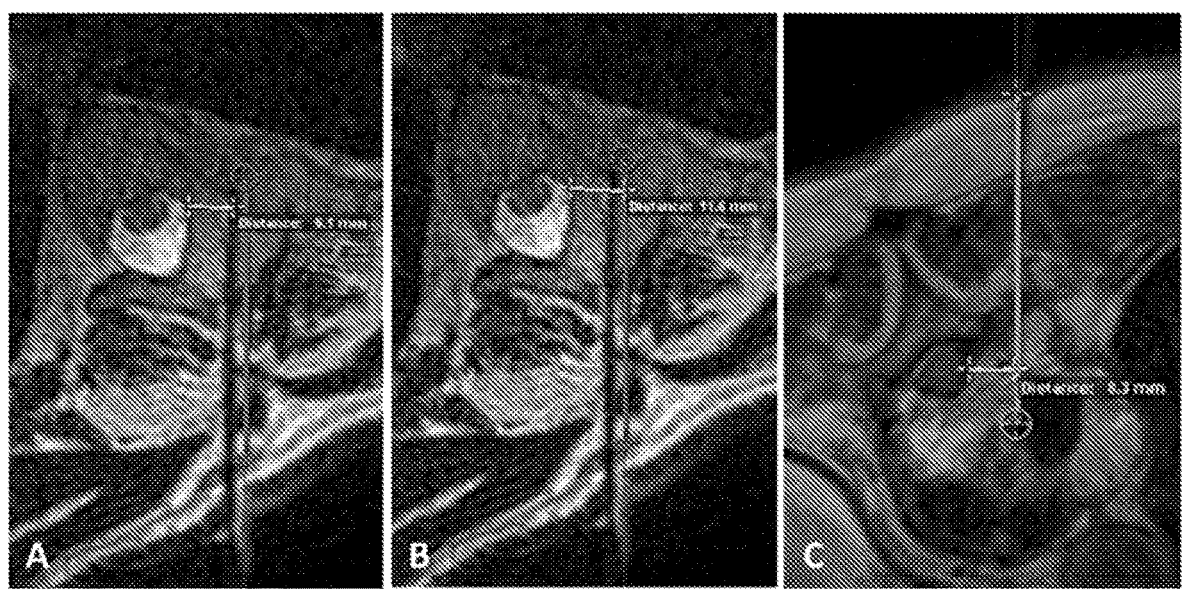
FIG. 16 shows MRI images of the patient during subsequent steps of the method of FIG. 12.

Once the navigated Jamishidi reaches its final position, a negative offset enough to reach the skin level is placed and a screenshot of the navigation monitor is saved. This represents the trajectory predicted by the navigation software from the entry point in the skin, to the target in the epidural space. The Jamishidi is exchanged and the patient is prepared for the localization scans [56]. T2 weighted MRI sequences reconstructed to the exact axial plane of each plastic access cannula are obtained. These images are fused to the corresponding final screenshot of the each predicted trajectory using the navigation software (Brainlab, Inc.). The shortest distance between the predicted and the actual fiber trajectory in relation to the dural edge at the level of the spinal canal is measured in millimeters (panels A and B of FIG. 16). Radial error (FIG. 16) was determined by measuring the tangential distance between the predicted and the real fiber position in the same axial plane. Laser catheters overlapping the desired trajectory were considered on target, with a radial error of zero, as described by Attaar et al. [59].

Statistical Analysis

Statistical analyses were performed with SPSS (IBM SPSS, Chicago, Ill.), using paired Student's t-tests for the measurement between the predicted and the real distance from the closest point of the probe to the dura. Wilcoxon signed rank tests assessed the median changes in thickness of epidural tumor and change in the ESCC classification. A $p$ value<0.05 was accepted as statistically significant.

Results

A total of 13 patients, 8 male and 5 females, with median age of 60 years (range 46-81 years), underwent percutaneous placement of a total of 49 laser catheters in multiple spine levels for treatment of epidural tumor (Table 4 below). All cases were performed under general anesthesia in the prone position. No morbidity was associated with the placement of the laser catheters or the thermal ablation, and the median hospital stay was 1 day (range 1-10). A total of 5 patients underwent SSRS after the laser ablation, one patient had cEBRT and 7 individuals had SLITT as salvage therapy not followed by radiation. The median image follow up was 2.1 months (range 0.3-5.4 months).

TABLE 4

Patient Demographics Enrolled in Study 2

| Case | Age/sex | Primary tumor | Level | Pre-OP KPS (%) | SINS score | Hospital stay (days) | Type and time from sLITT to radiation (days) | Radiation dose (Gy/Fr) | Remark |
|---|---|---|---|---|---|---|---|---|---|
| 1 | 76/M | Thyroid | T6, 7 | 90 | 6 | 1 | n/a | n/a | Prior cEBRT, SSRS |
| 2 | 40/M | Colon | T2 | 70 | 8 | 2 | n/a | n/a | Prior cEBRT, SSRS |
| 3 | 63/M | RCC | T8, 9 | 50 | 10 | 1 | n/a | n/a | Prior cEBRT, SSRS |
| 4 | 56/M | Lung | T2 | 60 | 14 | 5 | cEBRT, 4 | 30/10 | Perc. Stab. T1-T3 |
| 5 | 81/F | Lung | L1 | 40 | 13 | 5 | SSRS, 10 | 27/3 | Prior cEBRT, Perc. Stab. T12-L2 |
| 6 | 46/F | Thyroid | T2 | 80 | 7 | 1 | SSRS, 3 | 24/1 | |
| 7 | 63/F | Lung | T4, 5, 6 | 40 | 16 | 10 | n/a | n/a | Prior cEBRT, Perc Stab T2/3 to T7/8 |
| 8 | 68/F | Melanoma | T4 | 80 | 6 | 1 | n/a | n/a | Prior SSRS |
| 9 | 58/M | RCC | T2, 3 | 90 | 6 | 1 | SSRS, 6 | 27/3 | |
| 10 | 53/M | Lung | T2 | 70 | 10 | 1 | n/a | n/a | Prior cEBRT, SSRS |
| 11 | 64/M | Thyroid | T2 | 80 | 8 | 1 | SSRS, 6 | 18/1 | |
| 12 | 52/M | SCC tongue | T7, 8 | 80 | 6 | 1 | SSRS, 4 | 27/3 | |
| 13 | 60/F | Thyroid | T11 | 40 | 13 | 4 | n/a | n/a | Perc Stab T10-L2 Prior cEBRT |

RCC, renal cell carcinoma;
SCC, squamous cell carcinoma;
n/a, not available;
KPS, karnofsky performance scale;
SINS, spine instability neoplastic score;
OP, operation;
SSRS, spinal stereotactic radiosurgery;
cEBRT, conventional external beam radiotherapy Four patients had spinal instability, with a SINS score higher than 12 and were treated with placement of percutaneous pedicle screws. Three of those cases were performed at the same time of ablation using image guidance based on MRI (cases 4, 5 and 13). One case required a long segment stabilization (case 7) and was performed in a separate operation 1 day after the sLITT.

In order to quantify the improvement based on the ESCC score, we converted each category to a number. The median pre-operative score was 4 (range 3-5), which was significantly higher than the median score of 2.5 (range 0-5), at 2-month post treatment (p=0.04, Wilcoxon test).

Evaluation of Accuracy

The fiducial registration demonstrated excellent surface accuracy with a margin of error so low that we were not able to measure the discrepancy from the predicted location of the tip of the needle in the navigation screen and the real position in the surface of the skin, both on axial and sagittal planes (FIG. 10).

MRI images provided excellent visualization of the spinal cord and the epidural tumor in all cases. The median distance from the dura predicted by the navigation was 7.0 mm (95% CI XY), which was not different than the real median distance of the fiber of 6.7 mm (95% CI zw), p=0.04 (Table 5 below).

TABLE 5
Detail of Treatment Parameters in 13 Patients Performed Laser Interstitial Thermotherapy

| case | Pre-op ESCC | Post-op ESCC | Number of fibers | Average predicted distance from the fibers to dura (mm) | Average real distance from the fibers to dura (mm) | Average Radial error (mm) | Interval of image follow up (months) |
|---|---|---|---|---|---|---|---|
| 1 | 3 | 1b | 4 | 7.0 | 7.7 | 0.7 | 5.4 |
| 2 | 2 | 1c | 3 | 4.1 | 5.1 | 1.0 | 3.1 |
| 3 | 3 | 3 | 8 | 7.5 | 7.1 | 0.7 | 4.3 |
| 4 | 3 | 1b | 2 | 6.2 | 7.4 | 1.2 | 2.0 |
| 5 | 2 | 2 | 3 | 7.0 | 6.6 | 0.4 | 2.1 |
| 6 | 2 | 2 | 3 | 7.1 | 8.4 | 1.4 | 1.7 |
| 7 | 2 | n/a | 4 | 5.8 | 5.8 | 0.0 | n/a |
| 8 | 2 | 1b | 4 | 10.4 | 9.9 | 0.5 | 2.0 |
| 9 | 1c | 0 | 5 | 7.5 | 6.4 | 1.2 | 2.2 |
| 10 | 2 | 3 | 3 | 6.2 | 7.0 | 0.8 | 2.1 |
| 11 | 2 | 2 | 2 | 7.1 | 6.7 | 0.5 | 2.1 |
| 12 | 2 | n/a | 5 | 8.0 | 5.3 | 2.7 | n/a |
| 13 | 3 | n/a | 3 | 6.5 | 6.4 | 0.1 | n/a |
| Median | 2 | 1c | 3 | 7.0 | 6.7 | 0.7 | 2.1 | n/a, not available

The discrepancy in trajectory or radial error was 0.7 mm (range 0-2.9 mm), which did not correlate with adverse events or failure in the local control of the treated tumor at 2 months follow up.

Discussion

A multitude of spinal interventions are traditionally guided by conventional 2D fluoroscopic images, which has the advantage of portability, low cost and compatibility with the sterile operative field. However, the quality of image is subjected to deterioration in patients with severe osteoporosis, morbid obesity and most importantly, complex oblique trajectories are not properly imaged in the 2D plane. Given these limitations, image guidance for spinal procedures was developed based on CT images, which are ideal for delineation of bony structures and has become widely utilized for placement of posterior segmental instrumentation for which a series of surgical tools have been developed and adapted.

We have previously reported our method to place laser catheters to perform thermal ablation of epidural tumors [18]. Briefly, a pre-operative CT (obtained with the patient supine), was uploaded to the navigation system, and overlaid with an AP and lateral fluoroscopic image (obtained with the patient in the operative position). Computer software performs the alignment and fusion of images and 2D and 3D models of the region of interest are created. This method has two big shortcomings: A) surface inaccuracy: as the pre-op CT images are acquired in prone position, the weight of the body compresses the soft tissue of the dorsal region against the spine. When patient is positioned to surgery, such compression is relieved resulting in a significant mismatch precluding verification of accuracy of the image guidance. B) Poor visualization of the spinal cord, especially in cases of significant epidural compression.

The utilization of MRI as guidance for surgical procedures in the spine is very limited and few reports have been published [15-17]. A significant limitation of this method is the incompatibility of surgical instruments since surgery occurs inside or near a high power magnetic field. Fritz et al. [60]. described the use of augmented reality in which intraoperative MR images are uploaded to planning software. A frame is positioned over the region of interest and a liquid crystal display is used for passive projection of the MRI images in a semitransparent mirror over the dorsal region of the subject. The surgeon can guide a bone needle based on the entry point and the target projected on the patient skin. The final error of this complex set-up was 6.1±1.9 mm on the target for vertebroplasties [61] and 4.3±1.2 mm for the vertebral body biopsies [60]. These were both experimental studies with cadavers and the cost and the feasibility of this method is yet unknown.

Using MRI for placement of the laser catheters provides several advantages over our previously described technique: 1—Verification of accuracy of image guidance on the skin surface; 2—Planning the proper trajectory from the surface, minimizing the length of the skin incisions; 3—Excellent visualization of the spinal cord, even in cases of severe compression, enabling safe positioning of the catheters in the epidural space.

Our method takes advantage of standard fiducial markers, which are placed over the dorsal region. As a requirement for registration, these markers have to be visible in the scan, therefore the MRI coil has to be positioned above those fiducials. As the skin of the dorsal region is very loose, it is imperative to avoid displacement of the markers after the MRI is completed since even minor changes in position will result in inaccurate registration. To overcome these limitations, we introduced the use of a plastic cradle to support the MRI coil above the fiducials avoiding contact with them. This step is extremely important and we recommend careful observation of the cradle as the patient is transported in and out of the MRI scanner.

It has been our experience that the ideal MRI sequence for fiducial registration is T2 without fat saturation. This sequence allows excellent visualization of the CSF and the spinal cord and is less susceptible to motion degradation due to respiratory movements. Once the registration sequence is exported to the planning software, we recommend that the reference point for registration to be placed 1 mm below the fiducial, to compensate for the displacement of the dorsal skin associated with the "wiggling" of the registration wand at the time of surface matching of the fiducials.

Unfortunately, the current navigation hardware is not compatible with the magnetic field and the patient needs to be removed from the magnet for the fiber implantation. We take advantage of the iMRI transfer table which allows minimal manipulation of the patient during this process. Registration of the fiducials requires placement of a reference array, which we suture to the dorsal skin at least 1 foot away from the fiducial markers. We avoid performing a skin incision to attach the array to a spinous process, since this maneuver stretches the skin and creates displacement of the fiducials. Similarly, surgical draping needs to be loose and not attached to the skin, to avoid displacement of the fiducials or the array. Lastly, during fiber placement, it is imperative that the surgeon and the assistant do not touch the dorsal region of the patient to avoid displacement of the array and complete loss of accuracy.

Once the navigated Jamishidi is registered, we double check its accuracy before it is advanced towards the spinal cord. It has been our experience that surface accuracy predicts accuracy of the needle at the target. However, we do perform an AP fluoroscopic image to confirm needle position based on the pedicle of an uninvolved adjacent level as a reference for the limits of the spinal canal.

We have performed placement of 49 laser fibers without any morbidity. MRI guidance has significantly improved our workflow since visualization of the spinal cord has added an extra degree of confidence, reducing the need for additional confirmatory fluoroscopic images during needle advancement. We estimate an intraoperative timing of implantation of 15 minutes per fiber. Our results estimate a median radial error or discrepancy between the predicted and the actual trajectory of the navigated needle to be of 0.7 mm (range 0-2.7), which is similar to the data reported for stereotactic placement in cranial procedures [59]. Since we aim for a distance of 5-6 mm lateral to the dura, this margin of error is acceptable. We use the inline or trajectory axial view to track the needle as it is advanced towards the target. Once the needle is docked on the lamina, we release the navigated needle in order to make adjustments to the trajectory if necessary. We recommend against forcing corrections as the needle is advanced. Since each fiber is positioned free hand, we believe that most of our discrepancies between the predicted and the real position of the needle occurred because we had the impression of a different trajectory as we were manipulating the needle to the desired angle during advancement trough the lamina or pedicle. Once we reached the final position, release of the needle correlated with a slightly different angle, therefore explaining some of the cases of higher radial error. Another source of error is the unnoticed development of a subcutaneous hematoma or tension of the skin as the needle is introduced in oblique angles, displacing the reference array. This problem would be easily overcome with development of a non-ferromagnetic array, which could be securely attached to the spinous process and scanned in conjunction with the fiducials prior to registration.

Our method allowed re-registration of the fiducials, since we outlined them with a marking pen prior to the registration scan. This added the ability to use navigation for placement of the posterior segmental instrumentation after the laser ablation was completed. Although, this task could be easily achieved with fluoroscopy, navigation helped expedite the workflow inside the iMRI room.

An evaluation of the effectiveness of the laser ablations in controlling the epidural tumor is beyond the scope of this report and will be the focus of future publications. In the short follow up of our series, we have demonstrated good clinical local control in 11 out of 13 patients, where the median ESCC decreased one point from 2 to 1c. A total of 7 patients had sLITT as a salvage procedure, having already failed prior surgical and radiation treatments, among those, two failed to improve the epidural spinal cord compression. All cases were associated with a short hospital stay and we believe patients were able to resume oncologic treatment faster than if they were submitted to a standard open surgical decompression and stabilization, especially the individuals with a KPS lower than 60% where the added surgical morbidity would be excessive.

Conclusion

We demonstrate the feasibility and accuracy of using intraoperative MR images as a tool for image guidance in spinal procedures. To our knowledge this is the first report of such use and in our hands, it has been proven to be accurate and reliable for placement of the laser catheters and facilitating the placement of percutaneous stabilization in the same procedure. We believe this method can be used for other applications including biopsies, drainage of cysts or abscesses.

All of the devices, apparatus, systems, kits and/or methods disclosed and claimed herein can be made and executed without undue experimentation in light of the present disclosure. While the devices, apparatus, systems and methods of this invention have been described in terms of particular embodiments, it will be apparent to those of skill in the art that variations may be applied to the devices, apparatus, systems and/or methods in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

The contents of the following references are incorporated by reference herein:

1. Gilbert, R. W., J. H. Kim, and J. B. Posner, *Epidural spinal cord compression from metastatic tumor: diagnosis and treatment.* Ann Neurol, 1978. 3(1): p. 40-51.
2. Young, R. F., E. M. Post, and G. A. King, *Treatment of spinal epidural metastases. Randomized prospective comparison of laminectomy and radiotherapy.* J Neurosurg, 1980. 53(6): p. 741-8.
3. Bilsky, M. and M. Smith, *Surgical approach to epidural spinal cord compression.* Hematol Oncol Clin North Am, 2006. 20(6): p. 1307-17.
4. Latini, P., et al., *Role of radiotherapy in metastatic spinal cord compression: preliminary results from a prospective trial.* Radiother Oncol, 1989. 15(3): p. 227-33.
5. Rades, D., et al., *A prospective evaluation of two radiotherapy schedules with 10 versus 20 fractions for the treatment of metastatic spinal cord compression: final results of a multicenter study.* Cancer, 2004. 101(11): p. 2687-92.
6. Laufer, I., et al., *The NOMS framework: approach to the treatment of spinal metastatic tumors.* Oncologist, 2013. 18(6): p. 744-51.
7. Rades, D., J. H. Karstens, and W. Alberti, *Role of radiotherapy in the treatment of motor dysfunction due to metastatic spinal cord compression: comparison of three different fractionation schedules.* Int J Radiat Oncol Biol Phys, 2002. 54(4): p. 1160-4.
8. Maranzano, E., et al., *Radiation therapy in metastatic spinal cord compression. A prospective analysis of 105 consecutive patients.* Cancer, 1991. 67(5): p. 1311-7.
9. Patchell, R. A., et al., *Direct decompressive surgical resection in the treatment of spinal cord compression caused by metastatic cancer: a randomised trial.* Lancet, 2005. 366(9486): p. 643-8.
10. Wang, X. S., et al., *Stereotactic body radiation therapy for management of spinal metastases in patients without spinal cord compression: a phase 1-2 trial.* Lancet Oncol, 2012. 13(4): p. 395-402.
11. Gerszten, P. C., E. Mendel, and Y. Yamada, *Radiotherapy and radiosurgery for metastatic spine disease: what are the options, indications, and outcomes?* Spine (Phila Pa. 1976), 2009. 34(22 Suppl): p. S78-92.
12. Yamada, Y., et al., *High-dose, single-fraction image-guided intensity-modulated radiotherapy for metastatic spinal lesions.* Int J Radiat Oncol Biol Phys, 2008. 71(2): p. 484-90.
13. Gerszten, P. C., et al., *Radiosurgery for spinal metastases: clinical experience in 500 cases from a single institution.* Spine (Phila Pa. 1976), 2007. 32(2): p. 193-9.
14. Gerszten, P. C., et al., *Stereotactic radiosurgery for spinal metastases from renal cell carcinoma.* J Neurosurg Spine, 2005. 3(4): p. 288-95.
15. Sahgal, A., et al., *Stereotactic body radiotherapy for spinal metastases: current status, with a focus on its application in the postoperative patient.* J Neurosurg Spine, 2011. 14(2): p. 151-66.
16. Nguyen, Q. N., et al., *Management of spinal metastases from renal cell carcinoma using stereotactic body radiotherapy.* Int J Radiat Oncol Biol Phys, 2010. 76(4): p. 1185-92.
17. Chang, E. L., et al., *Phase I/II study of stereotactic body radiotherapy for spinal metastasis and its pattern of failure.* J Neurosurg Spine, 2007. 7(2): p. 151-60.
18. Bilsky, M. H., I. Laufer, and S. Burch, *Shifting paradigms in the treatment of metastatic spine disease.* Spine (Phila Pa. 1976), 2009. 34(22 Suppl): p. S101-7.
19. Moussazadeh, N., et al., *Separation surgery for spinal metastases: effect of spinal radiosurgery on surgical treatment goals.* Cancer Control, 2014. 21(2): p. 168-74.
20. Laufer, I., et al., *Local disease control for spinal metastases following "separation surgery" and adjuvant hypofractionated or high-dose single-fraction stereotactic radiosurgery: outcome analysis in 186 patients.* J Neurosurg Spine, 2013. 18(3): p. 207-14.
21. Akeboshi, M., et al., *Percutaneous radiofrequency ablation of lung neoplasms: initial therapeutic response.* J Vasc Intery Radiol, 2004. 15(5): p. 463-70.
22. Yamakado, K., et al., *Percutaneous radiofrequency ablation of liver neoplasms adjacent to the gastrointestinal tract after balloon catheter interposition.* J Vasc Intery Radiol, 2003. 14(9 Pt 1): p. 1183-6.

23. Rosenthal, D. and M. R. Callstrom, *Critical review and state of the art in interventional oncology: benign and metastatic disease involving bone*. Radiology, 2012. 262(3): p. 765-80.
24. Nakatsuka, A., et al., *Percutaneous radiofrequency ablation of painful spinal tumors adjacent to the spinal cord with real-time monitoring of spinal canal temperature: a prospective study*. Cardiovasc Intervent Radiol, 2009. 32(1): p. 70-5.
25. Ahrar, K. and R. J. Stafford, *Magnetic resonance imaging-guided laser ablation of bone tumors*. Tech Vasc Interv Radiol, 2011. 14(3): p. 177-82.
26. Bilsky, M. H., et al., *Reliability analysis of the epidural spinal cord compression scale*. J Neurosurg Spine, 2010. 13(3): p. 324-8.
27. Fisher, C. G., et al., *A novel classification system for spinal instability in neoplastic disease: an evidence-based approach and expert consensus from the Spine Oncology Study Group*. Spine (Phila Pa. 1976), 2010. 35(22): p. E1221-9.
28. Akeyson, E. W. and I. E. McCutcheon, *Single-stage posterior vertebrectomy and replacement combined with posterior instrumentation for spinal metastasis*. J Neurosurg, 1996. 85(2): p. 211-20.
29. Fourney, D. R., et al., *Use of pedicle screw fixation in the management of malignant spinal disease: experience in 100 consecutive procedures*. J Neurosurg, 2001. 94(1 Suppl): p. 25-37.
30. Molina, C. A., Z. L. Gokaslan, and D. M. Sciubba, *Diagnosis and management of metastatic cervical spine tumors*. Orthop Clin North Am, 2012. 43(1): p. 75-87, viii-ix.
31. Omeis, I., et al., *The use of expandable cages in patients undergoing multilevel corpectomies for metastatic tumors in the cervical spine*. Orthopedics, 2010. 33(2): p. 87-92.
32. Maranzano, E., et al., *Short-course radiotherapy (8 Gy×2) in metastatic spinal cord compression: an effective and feasible treatment*. Int J Radiat Oncol Biol Phys, 1997. 38(5): p. 1037-44.
33. Rades, D., et al., *Dose escalation for metastatic spinal cord compression in patients with relatively radioresistant tumors*. Int J Radiat Oncol Biol Phys, 2011. 80(5): p. 1492-7.
34. Maranzano, E., R. Bellavita, and R. Rossi, *Radiotherapy alone or surgery in spinal cord compression? The choice depends on accurate patient selection*. J Clin Oncol, 2005. 23(32): p. 8270-2; author reply 8272-4.
35. Garg, A. K., et al., *Prospective evaluation of spinal reirradiation by using stereotactic body radiation therapy: The University of Texas MD Anderson Cancer Center experience*. Cancer, 2011. 117(15): p. 3509-16.
36. Carpentier, A., et al., *MR-guided laser-induced thermal therapy (LITT) for recurrent glioblastomas*. Lasers Surg Med, 2012. 44(5): p. 361-8.
37. Carpentier, A., et al., *Real-time magnetic resonance-guided laser thermal therapy for focal metastatic brain tumors*. Neurosurgery, 2008. 63(1 Suppl 1): p. ONS21-8; discussion ONS28-9.
38. Vogl, T. J., et al., *Colorectal cancer liver metastases: long-term survival and progression free survival after thermal ablation using magnetic resonance guided laser-induced interstitial thermotherapy in 594 patients: analysis of prognostic factors*. Invest Radiol, 2014. 49(1): p. 48-56.
39. McNichols, R. J., et al., *MR thermometry-based feedback control of laser interstitial thermal therapy at 980 nm*. Lasers Surg Med, 2004. 34(1): p. 48-55.
40. Curry, D. J., et al., *MR-guided stereotactic laser ablation of epileptogenic foci in children*. Epilepsy Behav, 2012. 24(4): p. 408-14.
41. Adapon B D, Legada B D, Jr., Lim E V, Silao J V, Jr., Dalmacio-Cruz A. CT-guided closed biopsy of the spine. *Journal of computer assisted tomography*. February 1981; 5(1):73-78.
42. Bourgeois A C, Faulkner A R, Bradley Y C, et al. Improved Accuracy of Minimally Invasive Transpedicular Screw Placement in the Lumbar Spine With 3-Dimensional Stereotactic Image Guidance: A Comparative Meta-Analysis. *Journal of spinal disorders & techniques*. November 2015; 28(9):324-329.
43. Smitherman S M, Tatsui C E, Rao G, Walsh G, Rhines L D. Image-guided multilevel vertebral osteotomies for en bloc resection of giant cell tumor of the thoracic spine: case report and description of operative technique. *European spine journal: official publication of the European Spine Society, the European Spinal Deformity Society, and the European Section of the Cervical Spine Research Society*. June 2010; 19(6):1021-1028.
44. Chang B K, Timmerman R D. Stereotactic body radiation therapy: a comprehensive review. *American journal of clinical oncology*. December 2007; 30(6):637-644.
45. Tabaraee E, Gibson A G, Karahalios D G, Potts E A, Mobasser J P, Burch S. Intraoperative cone beam-computed tomography with navigation (O-ARM) versus conventional fluoroscopy (C-ARM): a cadaveric study comparing accuracy, efficiency, and safety for spinal instrumentation. *Spine*. Oct. 15, 2013; 38(22):1953-1958.
46. Rahmathulla G, Nottmeier E W, Pirris S M, Deen H G, Pichelmann M A. Intraoperative image-guided spinal navigation: technical pitfalls and their avoidance. *Neurosurgical focus*. March 2014; 36(3):E3.
47. Kim T T, Drazin D, Shweikeh F, Pashman R, Johnson J P. Clinical and radiographic outcomes of minimally invasive percutaneous pedicle screw placement with intraoperative CT (O-arm) image guidance navigation. *Neurosurgical focus*. March 2014; 36(3):E1.
48. Moriarty T M, Quinones-Hinojosa A, Larson P S, et al. Frameless stereotactic neurosurgery using intraoperative magnetic resonance imaging: stereotactic brain biopsy. *Neurosurgery*. November 2000; 47(5):1138-1145; discussion 1145-1136.
49. Hatiboglu M A, Weinberg J S, Suki D, et al. Impact of intraoperative high-field magnetic resonance imaging guidance on glioma surgery: a prospective volumetric analysis. *Neurosurgery*. June 2009; 64(6):1073-1081; discussion 1081.
50. Cui Z, Pan L, Song H, et al. Intraoperative MRI for optimizing electrode placement for deep brain stimulation of the subthalamic nucleus in Parkinson disease. *Journal of neurosurgery*. January 2016; 124(1):62-69.
51. Yeniaras E, Fuentes D T, Fahrenholtz S J, et al. Design and initial evaluation of a treatment planning software system for MRI-guided laser ablation in the brain. *International journal of computer assisted radiology and surgery*. July 2014; 9(4):659-667.
52. Missios S, Bekelis K, Barnett G H. Renaissance of laser interstitial thermal ablation. *Neurosurgical focus*. March 2015; 38(3):E13.
53. Woodard E J, Leon S P, Moriarty T M, Quinones A, Zamani A A, Jolesz F A. Initial experience with intraoperative magnetic resonance imaging in spine surgery. *Spine*. Feb. 15, 2001; 26(4):410-417.
54. Takahashi S, Morikawa S, Saruhashi Y, Matsusue Y, Kawakami M. Percutaneous transthoracic fenestration of an intramedullary neurenteric cyst in the thoracic spine with intraoperative magnetic resonance image navigation and thoracoscopy. *Journal of neurosurgery. Spine*. November 2008; 9(5):488-492.
55. Takahashi S, Saruhashi Y, Odate S, Matsusue Y, Morikawa S. Percutaneous aspiration of spinal terminal ventricle cysts using real-time magnetic resonance imaging and navigation. *Spine*. Mar. 15, 2009; 34(6):629-634.
56. Tatsui C E, Stafford R J, Li J, et al. Utilization of laser interstitial thermotherapy guided by real-time thermal MRI as an alternative to separation surgery in the management of spinal metastasis. *Journal of neurosurgery. Spine*. October 2015; 23(4):400-411.
57. Ghia A J, Rebueno N C, Li J, Brown P D, Rhines L D, Tatsui C E. The use of image guided laser interstitial thermotherapy to supplement spine stereotactic radiosurgery to manage metastatic epidural spinal cord compression: Proof of concept and dosimetric analysis. *Practical radiation oncology*. Nov. 11, 2015.
58. Fourney D R, Frangou E M, Ryken T C, et al. Spinal instability neoplastic score: an analysis of reliability and validity from the spine oncology study group. *Journal of clinical oncology: official journal of the American Society of Clinical Oncology*. Aug. 1, 2011; 29(22):3072-3077.
59. Attaar S J, Patel N V, Hargreaves E, Keller I A, Danish S F. Accuracy of Laser Placement With Frameless Stereotaxy in Magnetic Resonance-Guided Laser-Induced Thermal Therapy. *Neurosurgery*. Aug. 14, 2015.
60. Fritz J, P U T, Ungi T, et al. Augmented reality visualization using image overlay technology for MR-guided interventions: cadaveric bone biopsy at 1.5 T. *Investigative radiology*. June 2013; 48(6):464-470.
61. Fritz J, P U T, Ungi T, et al. MR-guided vertebroplasty with augmented reality image overlay navigation. *Cardiovascular and interventional radiology*. December 2014; 37(6): 1589-1596.

The invention claimed is:

1. A method for applying thermal energy to a target tissue in a region of interest, the method comprising:
coupling a plurality of fiducial markers to tissue proximal to the region of interest;
obtaining a magnetic resonance image (MRI) of the region of interest;
registering the plurality of fiducial markers with a stereotactic image guidance system;
verifying surface accuracy of the stereotactic image guidance system;
inserting an MRI-compatible instrument into the region of interest;
verifying sub-surface accuracy of the stereotactic image guidance system;
inserting a laser fiber into the target tissue in the region of interest;
applying thermal energy to the target tissue; and
monitoring temperature in the target tissue and the region of interest, wherein the MRI-compatible instrument is a needle comprising a removable trocar and wherein the method further comprises:
removing the removable trocar from the needle and inserting a wire through the needle; and
inserting a cannula over the wire, wherein inserting a laser fiber into the target tissue in the region of interest comprises inserting the laser fiber through the cannula.

2. The method of claim 1 wherein the target tissue is a tumor.

3. The method of claim 1 wherein the region of interest is proximal to a spinal cord, an eye, or a lung.

4. The method of claim 1 wherein the region of interest comprises the dura mater.

5. The method of claim 1 wherein a portion of the plurality of fiducial markers each comprise an aperture and wherein the method further comprises marking locations of each aperture on epidermal tissue proximal to the region of interest.

6. The method of claim 1 wherein verifying the surface accuracy of the stereotactic image guidance system comprises touching a second instrument to epidermal tissue proximal to the region of interest.

7. The method of claim 1 wherein the laser fiber has a diameter of less than 2.0 mm.

8. The method of claim 1 wherein the laser fiber comprises silica fiberoptic wire.

9. The method of claim 1 wherein the laser fiber is coupled to a laser generator configured to generate electromagnetic radiation having a wavelength between 600 and 1200 nm.

10. The method of claim 1 wherein monitoring temperature in the target tissue and the region of interest comprises an application of magnetic resonance thermography.

11. The method of claim 1 further comprising increasing oxygen levels in blood of the patient prior to applying thermal energy to the target tissue.

12. The method of claim 11 further comprising holding mechanical ventilation while monitoring temperature in the target tissue and the region of interest.

13. The method of claim 1 further comprising automatically stopping application of thermal energy to the target tissue if a temperature in the target tissue or a temperature in the region of interest reach a predetermined value.

14. A method for applying thermal energy to a target tissue in a region of interest, the method comprising:
coupling a plurality of fiducial markers to tissue proximal to the region of interest;
obtaining a magnetic resonance image (MRI) of the region of interest;
registering the plurality of fiducial markers with a stereotactic image guidance system;
verifying surface accuracy of the stereotactic image guidance system;
inserting an MRI-compatible instrument into the region of interest;
verifying sub-surface accuracy of the stereotactic image guidance system;
inserting a laser fiber into the target tissue in the region of interest;
applying thermal energy to the target tissue; and
monitoring temperature in the target tissue and the region of interest, wherein coupling the plurality of fiducial markers to tissue proximal to the region of interest comprises applying an adhesive sheet to epidermal tissue and wherein the method further comprises removing a portion of the adhesive sheet prior to inserting the MRI-compatible instrument into the region of interest.

* * * * *